US012685441B2

(12) United States Patent
Penfold

(10) Patent No.: US 12,685,441 B2
(45) Date of Patent: Jul. 21, 2026

(54) METHOD OF DETECTING ONE OR MORE CHANGE IN AN EYE AND DISEASE INDICATION OR DIAGNOSIS

(71) Applicant: EYE CO PTY LTD, Moruya (AU)

(72) Inventor: Philip Leslie Penfold, Moruya (AU)

(73) Assignee: EYE CO PTY LTD., New South Wales (AU)

( * ) Notice: Subject to any disclaimer, the term of this patent is extended or adjusted under 35 U.S.C. 154(b) by 408 days.

(21) Appl. No.: 18/256,758

(22) PCT Filed: Dec. 10, 2021

(86) PCT No.: PCT/AU2021/051480
§ 371 (c)(1),
(2) Date: Jun. 9, 2023

(87) PCT Pub. No.: WO2022/120437
PCT Pub. Date: Jun. 16, 2022

(65) Prior Publication Data
US 2024/0016380 A1     Jan. 18, 2024

(30) Foreign Application Priority Data
Dec. 11, 2020     (AU) ................................ 2020904628

(51) Int. Cl.
*A61B 3/12*          (2006.01)
*A61B 3/00*          (2006.01)
          (Continued)

(52) U.S. Cl.
CPC .......... *A61B 3/1241* (2013.01); *A61B 3/0025* (2013.01); *A61B 3/102* (2013.01);
          (Continued)

(58) Field of Classification Search
CPC ..... A61B 3/1241; A61B 3/0025; A61B 3/102; A61B 5/004; A61B 5/4082; A61B 5/7275;
          (Continued)

(56) References Cited

U.S. PATENT DOCUMENTS 8,303,115 B2     11/2012  Ribaric et al.
2012/0087864 A1*  4/2012  Mashima ........... A61K 31/5575
                                                    424/9.2
          (Continued)

FOREIGN PATENT DOCUMENTS

WO         2015/016290 A1     1/2015
WO      WO-2015013632 A1 *   1/2015   ........... G06T 7/0016
          (Continued)

*Primary Examiner* — Mohammed A Hasan
(74) *Attorney, Agent, or Firm* — Tarolli, Sundheim, Covell & Tummino LLP

(57)          ABSTRACT

A method of detecting one or mor change in an eye and method diagnosing or proving an indication of an eye disease or eye condition or a neurogenerative disease or condition, or a predisposition thereto are disclosed. The method of detection comprises comparing an image of the eye with at least one asynchronous image of the eye to thereby detect the one or more change in the eye wherein the change comprises a darkening or lightening in pigment of the Retinal Pigment Epithelium (RPE) in the macula. The method of diagnosing or providing an indication of an eye disease or eye condition or a neurodegenerative disease or condition or a predisposition thereto comprises the same comparison and when the change is detected, providing a diagnosis of indication of or predisposition to an eye disease or eye condition or a neurodegenerative disease or condition or a predisposition thereto.

21 Claims, 13 Drawing Sheets

(51) Int. Cl.

| | |
|---|---|
| *A61B 3/10* | (2006.01) |
| *A61B 5/00* | (2006.01) |
| *A61K 36/185* | (2006.01) |
| *G06T 7/00* | (2017.01) |

(52) U.S. Cl.

CPC ............ *A61B 5/004* (2013.01); *A61B 5/4082* (2013.01); *A61B 5/7275* (2013.01); *A61B 5/7282* (2013.01); *A61K 36/3482* (2024.05); *G06T 7/0016* (2013.01); *G06T 2207/10101* (2013.01); *G06T 2207/20032* (2013.01); *G06T 2207/20076* (2013.01); *G06T 2207/20084* (2013.01); *G06T 2207/30041* (2013.01)

(58) Field of Classification Search

CPC ....... A61B 5/7282; A61B 3/12; A61B 5/4848; A61B 5/4088; A61B 5/4842; A61B 2576/02; A61B 5/0022; G06T 7/0016; G06T 2207/10101; G06T 2207/20032; G06T 2207/20076; G06T 2207/20084; G06T 2207/30041; G06T 7/0014; G06T 7/30; A61K 45/06; A61K 31/573; A61K 36/185; A61K 36/3482; G16H 20/17; G16H 50/20; G16H 50/70; G16H 20/10; G16H 30/40; A61P 27/02

USPC ........................................................ 351/206

See application file for complete search history.

(56) References Cited

U.S. PATENT DOCUMENTS

| | | | | |
|---|---|---|---|---|
| 2016/0058617 | A1* | 3/2016 | Luttrull | ................ A61N 5/0613 606/5 |
| 2016/0206190 | A1* | 7/2016 | Reisman | .............. A61B 3/1225 |
| 2020/0320703 | A1* | 10/2020 | Farchione | .............. G06F 3/013 |
| 2020/0352963 | A1 | 11/2020 | Penfold | |
| 2021/0035301 | A1* | 2/2021 | Soares | ................ G06F 3/04883 |

FOREIGN PATENT DOCUMENTS

| | | | | |
|---|---|---|---|---|
| WO | 2015/016291 A1 | 2/2015 | | |
| WO | 2018/069768 A2 | 4/2018 | | |
| WO | 2019/191800 A1 | 10/2019 | | |
| WO | WO-2020160606 A1 * | 8/2020 | ............. | G06V 40/18 |

\* cited by examiner

*Figure 1B(ii)*

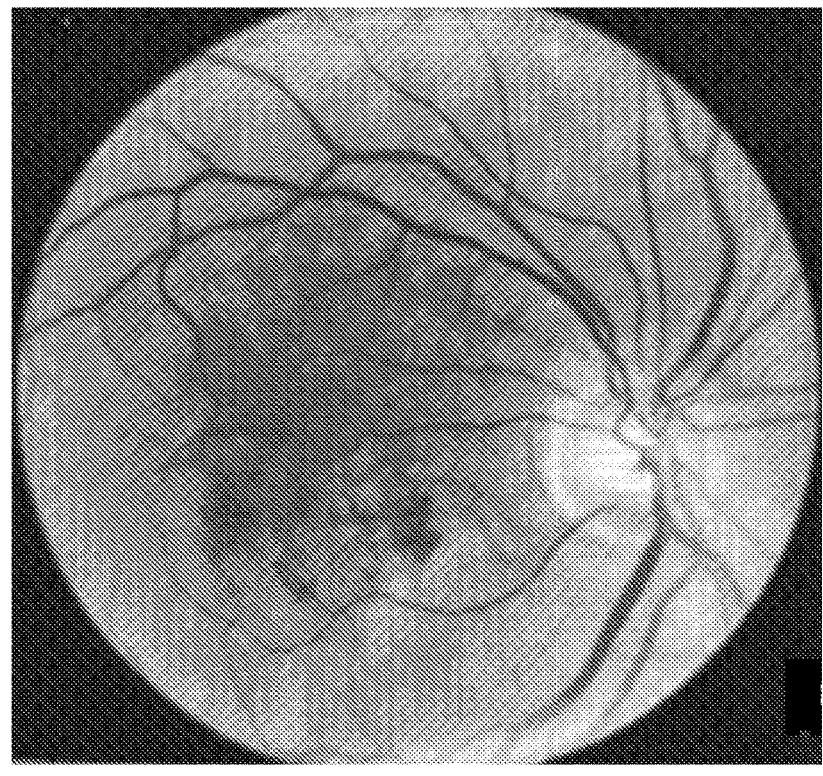
*Figure 1D(i)*
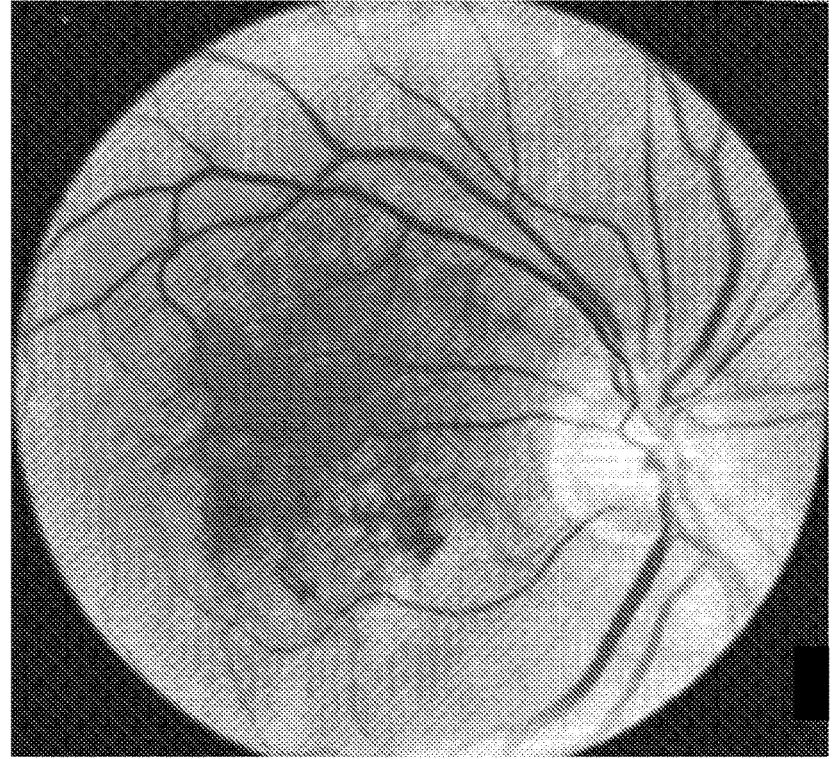
*Figure 1D(ii)*

*Figure 5B(ii)*

METHOD OF DETECTING ONE OR MORE CHANGE IN AN EYE AND DISEASE INDICATION OR DIAGNOSIS

FIELD OF THE INVENTION

The present invention relates to a method of detecting one or more change in an eye. More particularly, this invention relates to a method of detecting one or more change in an eye and providing a diagnosis or indication or an eye disease or eye condition or a predisposition thereto.

BACKGROUND TO THE INVENTION

Eye disease such as, age related macular degeneration (AMD), typically require a highly skilled practitioner to diagnose.

Typically, diagnosis of AMD relies on changes in the macula. Diagnosis of AMD is conventionally performed using visual tests, imaging techniques and/or histological testing. Visual tests which may be used include: dark adaptometry; contrast sensitivity testing; an Amsler grid; a Snellen chart; colour acuity and contrast sensitivity testing; and perimetry. Conventional imaging techniques that are used include ocular coherence tomography (OCT) and/or histological testing. Clinical examination of the eye can also be used wherein the appearance of drusen, yellow or white accumulations of extracellular material that build up between Bruch's membrane and the retinal pigment epithelium (RPE), can be a diagnostic indicator. Electroretinography can also be utilized.

The transition from dry to wet AMD can happen rapidly, and if left untreated, can lead to legal blindness in as little as six months. It is widely accepted that in dry macular degeneration, which occurs in 85 to 90 percent of AMD cases, drusen spots can be seen in Fundus photography. In wet macular degeneration, angiography can visualize the leakage of blood and proteins behind the macula.

WO 2015/013632, the publication of PCT/US2014/048222, to THE REGENTS OF THE UNIVERSITY OF MICHIGAN, teaches a method for automatically measuring changes in retinal, retinal pigment epithelial, or choroidal disease and includes retrieving a set of images of a fundus and selecting a plurality of images from the set of images. The plurality of images are co-registered and pre-processed such that the quality, contrast, and gain of each of the plurality of images is made similar. Then, a comparison is made between the plurality of images to determine a change in retinal, retinal pigment epithelial, or choroidal disease, wherein the change is determined based on various disease metrics.

WO 2020/160606, the publication of PCT/AU2020/050080, to COMMONWEALTH SCIENTIFIC AND INDUSTRIAL RESEARCH ORGINISATION, discloses a method for diagnostic imaging of a retina of a patient with diabetic retinopathy. A processor retrieves a first image of the retina captured at a first point in time and a second image of the retina captured at a second point in time after the first point in time. The processor aligns the first image to the second image to reduce an offset between non-pathologic retinal features in the first image and the second image and obtains image objects related to diabetic retinopathy in the first image and the second image. The processor then calculates a numerical pathology score indicative of a progression of the diabetic retinopathy by calculating a degree of change of the image objects.

WO 2018/069768 A2, the publication of PCT/IB2017/001399, TRANSLATUM MEDICUS, INC., elucidates a method for quantifying disease progression through retinal health assessment and management. The method comprises obtaining a first image of a retina or iris at a point in time; generating a first vascular map of the first image of the retina or the iris; obtaining a second image of the retina or the iris at a later point in time; generating a second vascular map of the second image of the retina or the iris; registering the first image and the second image on the basis of the first vascular map and the second vascular map; and displaying at least one difference between the registered first image and the second image to quantify a disease progression.

WO 2015/016290 and WO 2015/016291, the publications of PCT/JP2014/070146 and PCT/JP2014/070147, respectively, both to CANON KABUSHIKI KAISHA, disclose an image processing apparatus including a positioning unit configured to position multiple polarization-sensitive tomographic images corresponding to multiple tomographic luminance images, based on the plurality of tomographic luminance images obtained by photographing an object at different times; and a comparing unit configured to compare the images.

Improved methods of diagnosing an eye disease or condition are required.

The reference to any prior art in this specification is not, and should not be taken as, an acknowledgement or any form of suggestion that the prior art forms part of the common general knowledge.

SUMMARY OF THE INVENTION

The present invention is directed to a method of detecting one or more change in an eye. In a particular embodiment, this invention relates to a method of detecting one or more change in an eye and providing a diagnosis or indication or an eye disease or eye condition or a predisposition thereto.

In a first form, although it need not be the only or indeed the broadest form, the invention resides in a method of detecting one or more change in an eye, the method comprising:

comparing an image of the eye with at least one asynchronous image of the eye to thereby detect the one or more change in the eye wherein the change comprises a darkening or lightening in pigment of the Retinal Pigmented Epithelium (RPE) in the macula.

In a second form, the invention resides in a method of diagnosing or providing an indication of an eye disease or eye condition or a predisposition thereto or a neurodegenerative disease or condition or a predisposition thereto, the method comprising:

comparing an image of said eye with at least one asynchronous image of the eye to detect the one or more change in the eye wherein the change comprises a darkening or lightening in pigment of the Retinal Pigmented Epithelium (RPE) in the macula; and when the change is detected providing a diagnosis of, indication of or predisposition to an eye disease or eye condition or a neurodegenerative disease or condition or a predisposition thereto.

In a third form, invention resides in a computer program product comprising a non-transitory computer useable medium said computer program product comprising:

a computer usable medium and computer readable program code embodied on said computer usable medium for detecting one or more change in an eye, the computer readable code comprising:

computer readable program code devices (i) configured to cause the computer to compare an image of the eye with at least one asynchronous image of the eye to thereby detect the one or more change in the eye wherein the change comprises a darkening or lightening in pigment of the Retinal Pigmented Epithelium (RPE) and/or macula.

In a fourth form, the invention resides in a computer program product comprising a non-transitory computer useable medium said computer program product comprising:

a computer usable medium and computer readable program code embodied on said computer usable medium for diagnosing or providing an indication of an eye disease or eye condition or a predisposition thereto or a neurodegenerative disease or condition or a predisposition thereto, the computer readable code comprising:

computer readable program code devices (i) configured to cause the computer to compare an image of said eye with at least one asynchronous image of the eye to thereby detect the one or more change in the eye wherein the change comprises a darkening or lightening in pigment of the Retinal Pigmented Epithelium (RPE) and/or macula; and computer readable program code devices (ii) configured, when a change is detected, to cause the computer to provide a diagnosis of, indication of or prognosis of an eye disease or eye condition or a neurodegenerative disease or condition or a predisposition thereto.

In a fifth form, the invention provides a device for detecting one or more change in an eye, the device comprising:

a processor for comparing an image of the eye with at least one asynchronous image of the eye to thereby detect the one or more change in the eye wherein the change comprises a darkening or lightening in pigment of the Retinal Pigmented Epithelium (RPE) and/or macula.

In one embodiment of the first, third or fifth forms, the detected change may be diagnostic of, indicative of or prognostic of an eye disease or eye condition or predisposition thereto.

In a sixth form, the invention resides in a device for diagnosing, indicating or providing a prognosis of an eye disease or eye condition or a predisposition thereto or a neurodegenerative disease or condition or a predisposition thereto, the device comprising:

a device for comparing an image of said eye with at least one asynchronous image of the eye to detect the one or more change in the eye wherein the change comprises a darkening or lightening in pigment of the Retinal Pigmented Epithelium (RPE) and/or macula; and when a change is detected providing a diagnosis of, indication of or predisposition to an eye disease or eye condition or a neurodegenerative disease or condition or a predisposition thereto.

In a seventh form, the invention resides in a computer system comprising the device of the fifth form or the sixth form operatively connected a network. The device of the fifth form or the sixth form may receive the image and the at least one asynchronous image through the network. The image and the at least one asynchronous image received through the network may be received from a database.

According to any one of the above forms, the darkening or lightening may comprise one or both of a pigmentary disturbance and mottling. The darkening or lightening may occur in either direction from one point in time to another point in time. An area that has previously had an increase in pigmentation may later have a decrease in pigmentation. An area that has previously had a decrease in pigmentation may later have an increase in pigmentation.

According to one embodiment of any of the above forms, the change in pigment may indicate neovascularization or a new blood vessel. The detected change in pigment may not be penetrative.

In one embodiment of any one of the above forms, the change may be in absence of drusen or any change in drusen.

According to another embodiment of any one of the above forms, the image and the asynchronous image comprise digital images.

According to yet another embodiment of any one of the above forms, the comparing may be by one or more processing element. The processing element may comprise an electronic circuit, a microprocessor or an internal component of a microprocessor.

According to yet another embodiment of any one of the above forms, the comparing may be by an artificial intelligence. The artificial intelligence may comprise a neural network or artificial neural network such as a convolutional neural network; a deep neutral network or a deep convolutional neural network. The search may be of an entire image. The convolutional neural network may be an INCEPTION-RESNET-V2 network or based thereon.

In one embodiment of any one of the above forms, the neural network may comprise an object detection system. The object detection system may use a neural network based YOLO (you only look once) real time object detection architecture.

In another embodiment of any one of the above forms, the neural network may comprise an image classifier. The image classifier may comprise a neural network based on VGG (Visual Geometry Group) classifier. The classifier may receive the one or more digital image. The classifier may be pre-trained. The pre-training may comprise training on a data set. The output model of the network may be modified to identify only two classes: received digital images containing a detected change, i.e. positive, and received digital images not containing a detected change, i.e. negative. The classifier may have been trained by fine tuning on a training set of example images. The example images may comprise, more than one hundred, more than one thousand, more than a hundred thousand, or more than one million example digital images. The training set may comprise positive and negative labelled images. When the digital image is fed into the classifier network, the analysis may determine as output a confidence that the image is positive for the detected change. The determined confidence may comprise for example a confidence output of 0% which is very unlikely to show a detected change and a confidence output of 100% which is very likely to show a detected change. A threshold may be used to limit which images are deemed positive and which are deemed negative. The threshold may comprise a threshold value which may be dynamically adjusted so that a top margin of images are deemed positive and sent on for manual review. The top margin may comprise a top 5; 10; 15; 20; or 25% of received cropped images with respected to determined confidence.

According to any one of the above forms, the comparison may comprise a real time object detector. The real time object detector may identify the one or more change. The comparison may comprise a positive identification of the one or more change. The real time object detector may output a location of the detected one or more change in the digital image and optionally a confidence score the one or more change has been detected.

According to still embodiment of any one of the above forms, the comparing may comprise image registration. The image registration may comprise transforming the image and the at least one asynchronous image into one coordinate system.

According to one embodiment of any one of the above forms, the image and the at least one asynchronous image may be processed. The processing may include removing noise.

According to one embodiment of any one of the above forms, the comparing may comprise one or more of determining intensity levels; determining a distribution of gradient magnitude; determining intensity profile.

According to one embodiment of any one of the above forms, the change may be detected by comparing intensity levels. The change may be detected in one or more of the retina and the macula.

According to one embodiment of any one of the above forms, the invention may also include image pre-processing such as, color channel extraction, median filtering and/or Gaussian smoothing.

According to one embodiment of any one of the above forms, the image and the at least one asynchronous image comprise one or more 2-D image and/or one or more 3-D image. The one or more 2-D image may comprise a fundus image or an Optical Coherence Tomography (OCT) image. The one or more 3-D image may comprise one or more OCT image.

In another embodiment of any above forms, the method, device or system may further comprise monitoring a fellow eye of a subject with neovascularisation in the other retina with the method, computer program product, device or system according to any one of the above forms to confirm disease or condition progression or validate the method, computer program product, device or system of any one of the above forms.

In still another embodiment of any above forms, the change may be detected using an algorithm or methodology trained on one or more fellow eye of a subject with neovascularisation in the other retina. The training may be with the method, computer program product, device or system according to any one of the above forms.

In yet another embodiment of any of the above forms, the temporal changes detected may be used to diagnose, detect or indicate a likelihood of developing Alzheimer's disease or another neurodegenerative disease or condition such as, Parkinson's disease; Huntington's disease; Amyotrophic lateral sclerosis; and Batten disease. The neurodegenerative disease or condition may also comprise an encephalopathy such as, a transmissible spongiform encephalopathy.

In one embodiment of any above forms, one or more colour changes may be indicative of Alzheimer's disease or another neurodegenerative disease.

In one embodiment of any one of the above forms, an in vivo dye may be utilised to visualise inflammatory changes in the retina that allows diagnosis or an indication of Alzheimer's disease or another neurodegenerative disease or condition.

In yet another embodiment of any one of the above forms, the change may be associated with a marker of MHC class II proteins. The marker may comprise fluorescent tags for MHC or class II antigens or other inflammatory markers.

The one or more asynchronous image may be asynchronous by one day, one week, one fortnight, one month, one quarter, one half-year or one year.

The subject may be middle aged or older. Images may be collected from age 40, 45, 50, 55, 60, 65 or older.

The eye condition may comprise any eye condition such as, early or sub-clinical stages of an eye disease.

The eye disease may comprise any eye disease such as, macular degeneration, maculopathy including an age related maculopathy (ARM), age related macular degeneration (AMD) including both the dry (geographic atrophy) and wet (choroidal neovascularisation (CNV)), an exudative eye disease or condition, retinal pigment epithelium detachments (PED), forms of age related macular degeneration, a diabetic eye disease or condition including a diabetic retinopathy and diabetic macular oedema (DME), corneal neovascularisation, cyclitis, Hippel-Lindel disease, retinopathy of prematurity (also known as retrolental fibroplasia), pterygium, histoplasmosis, iris neovascularisation, glaucoma, glaucoma-associated neovascularisation, Purtcher's retinopathy, ocular hypertension, macular oedema, Coats' disease, uveitis including anterior uveitis, Sicca syndrome, hereditary diseases associated with increased extra-intracellular lipid storage/accumulation, juvenile macular degeneration, an ocular allergy and an ocular tumour. The ocular tumour may comprise a retinoblastoma and/or a melanoma.

The eye disease or condition may comprise a back of eye disease or condition, including an exudative back of eye exudative disease or condition. The back of eye disease or condition may comprise an eye disease or condition involving the retina, macular and/or fovea in the posterior region of the eye. Examples of back of eye diseases include macular oedema, such as clinical macular oedema or angiographic cystoid macular oedema arising from various aetiologies, such as diabetes, exudative macular degeneration and macula oedema arising from laser treatment of the retina, retinal ischemia and choroidal neovascularisation, a retinal disease, an inflammatory disease, uveitis associated with neoplasms, such as retinoblastoma or psuedoglioma, neovascularisation following vitrectomy, a vascular disease and neovascularisation of the optic nerve. The retinal disease may be one or more of diabetic retinopathy, diabetic retinal oedema, retinal detachment, senile macular degeneration due to sub-retinal neovascularisation and myopic retinopathy. The vascular disease may be one or more of retinal ischemia, choroidal vascular insufficiency, choroidal thrombosis and neovascular retinopathies resulting from carotid artery ischemia.

In one embodiment of any one of the above forms, the eye disease or condition comprises dry AMD. Dry AMD may comprise early AMD and geographic atrophy (GA), distinct from exudative AMD.

In another embodiment of any one of the above forms, treatment comprises prophylactic treatment. The prophylactic treatment may comprise treatment to prevent dry AMD, treatment of a predisposition to dry AMD or treatment of a susceptibility to dry AMD. The predisposition or susceptibility may comprise an individual with a family history of an eye disease or condition such as, dry AMD.

The invention may find application to an exudative eye disease and/or condition, a back of the eye exudative eye disease and/or condition, age-related macular degeneration, wet age related macular degeneration, a diabetic macular oedema (DME), cystoid macular oedema (CMO); maculopathy; and/or an ocular tumour. The ocular tumour may comprise a retinoblastoma and/or a melanoma. The eye disease and/or condition may be a diabetic eye disease and/or condition. Other eye disease and/conditions include (non-infectious) conjunctivitis, anterior uveitis and an ocular allergy.

Accordingly, to one particular embodiment of any one of the above forms, the one or more eye disease or condition comprises age related macular degeneration (AMD). The AMD may comprise wet AMD.

According to any one of the above forms, said eye disease and/or condition may be an exudative eye disease and/or condition.

According to any one of the above forms, said eye disease and/or condition may be a back of the eye exudative eye disease and/or condition.

According to any one of the above forms, said eye disease and/or condition may be a diabetic macular oedema (DME), cystoid macular oedema (CMO); maculopathy; and/or an ocular tumour.

According to another particular embodiment of any one of the above forms, the one or more eye disease or condition comprises glaucoma.

According to any one of the above forms, said eye disease and/or condition may be a diabetic eye disease and/or condition.

Other eye disease and/conditions include (non-infectious) conjunctivitis, anterior uveitis and an ocular allergy.

According to any one of the above forms, when the one or more change is detected, one or more mineralocorticoid and/or one or more glucocorticoid or a therapeutically active analogue, derivative, homolog, pharmaceutically acceptable salt or conjugate thereof may be applied to the eye.

The one or more mineralocorticoid or a therapeutically active analogue, derivative, homolog, pharmaceutically acceptable salt or conjugate thereof may comprise one or more of: 11-desoxycortisone (11-DC); fludrocortisone; fludrocortisone acetate (FA); fludrocortisone acetonide; Deoxycorticosterone acetate (DA); Deoxycorticosterone (DS); or Aldosterone; or a therapeutically active analogue, derivative, homolog, pharmaceutically acceptable salt or conjugate thereof.

The one or more glucocorticoid or a therapeutically active analogue, derivative, homolog, pharmaceutically acceptable salt or conjugate thereof may comprise one or more of: cortisol, cortisone, prednisone, prednisolone, methylprednisolone, dexamethasone, betamethasone, triamcinolone, triamcinolone acetonide, beclometasone or a therapeutically active analogue, derivative, homolog, pharmaceutically acceptable salt or conjugate thereof.

The one or more mineralocorticoid and/or more glucocorticoid or a therapeutically active analogue, derivative, homolog, pharmaceutically acceptable salt or conjugate thereof may comprise one or more dual action compounds, wherein each dual action compound is capable of modulating the activity of both a mineralocorticoid receptor and a glucocorticoid receptor.

The dual action compound may comprise one or more of triamcinolone; triamcinolone acetonide; cortisol; cortisone; prednisone; prednisolone; methylprednisolone; fludrocortisone; fludrocortisone acetate; fludrocortisone acetonide; or a therapeutically active analogue, derivative, homolog, pharmaceutically acceptable salt or conjugate thereof.

In a particular embodiment the one or more mineralocorticoid or one or more glucocorticoid or a therapeutically active analogue, derivative, homolog, pharmaceutically acceptable salt or conjugate thereof comprises fludrocortisone or a therapeutically active analogue, derivative, homolog, pharmaceutically acceptable salt or conjugate thereof. The therapeutically active analogue, derivative, homolog, pharmaceutically acceptable salt or conjugate thereof may comprise one or more of fludrocortisone acetate and fludrocortisone acetonide.

In one particular embodiment, the one or more mineralocorticoid and/or one or more glucocorticoid or a therapeutically active analogue, derivative, homolog, pharmaceutically acceptable salt or conjugate thereof comprises triamcinolone acetonide or a therapeutically active analogue, derivative, homolog, pharmaceutically acceptable salt or conjugate thereof.

When the one or more mineralocorticoid and/or one or more glucocorticoid or a therapeutically active analogue, derivative, homolog, pharmaceutically acceptable salt or conjugate thereof comprises triamcinolone acetonide the concentration may comprise 3.0 to 5.0 mg/ml. In one particular embodiment the concentration may comprise 4.0 mg/ml.

In another particular embodiment of any of the above forms, the one or more mineralocorticoid and or one or more glucocorticoid or a therapeutically active analogue, derivative, homolog, pharmaceutically acceptable salt or conjugate thereof comprises triamcinolone and fludrocortisone or a therapeutically active analogue, derivative, homolog, pharmaceutically acceptable salt or conjugate of either. The therapeutically active analogue, derivative, homolog, pharmaceutically acceptable salt or conjugate thereof may comprise one or more of fludrocortisone acetate and fludrocortisone acetonide and triamcinolone acetonide.

In another embodiment of any above form, the one or more mineralocorticoid and/or one or more glucocorticoid or a therapeutically active analogue, derivative, homolog, pharmaceutically acceptable salt or conjugate thereof comprises a mixture of one or more mineralocorticoid or a therapeutically active analogue, derivative, homolog, pharmaceutically acceptable salt or conjugate thereof and one or more glucocorticoid or a therapeutically active analogue, derivative, homolog, pharmaceutically acceptable salt or conjugate thereof. The mixture may comprise: two or more mineralocorticoids or a therapeutically active analogue, derivative, homolog, pharmaceutically acceptable salt or conjugate thereof; two or more glucocorticoids or a therapeutically active analogue, derivative, homolog, pharmaceutically acceptable salt or conjugate thereof and/or one or more mineralocorticoid or a therapeutically active analogue, derivative, homolog, pharmaceutically acceptable salt or conjugate thereof and one or more glucocorticoids or a therapeutically active analogue, derivative, homolog, pharmaceutically acceptable salt or conjugate thereof.

In one embodiment of the first form, the method further comprises injecting the one or more mineralocorticoid and/or one or more glucocorticoid. The injection may comprise suprachoroidal injection.

In another embodiment of any one of the above forms, the one or more mineralocorticoid and/or one or more glucocorticoid is provided in a unit-dose formulation. The unit dose formulation may be provided in a pre-filled syringe. The pre-filled syringe may comprise two barrels. A first barrel may comprise the one or more mineralocorticoid and/or one or more glucocorticoid. A second barrel, different to the first barrel, may comprise one or more additional agent.

In another embodiment of any one of the above forms, one or more pharmaceutically acceptable carriers, diluents or excipients may be comprised such as, one or more surfactant or wetting agent.

In still another embodiment of any above form, the surfactant may comprise a polysorbate. The polysorbate may comprise one or more of polysorbate 20 and polysorbate 80. In a particular embodiment the surfactant comprises polysorbate 80.

In another embodiment of any above form, the pharmaceutically acceptable carrier, diluent or excipient may comprise carboxy methyl cellulose (CMC).

In one embodiment of any above form, the one or more mineralocorticoid and/or one or more glucocorticoid further comprises one or more of a pH adjustment composition and water for injection. The pH adjustment composition may comprise hydrochloric acid and/or sodium hydroxide.

In another embodiment of any above form the one or more mineralocorticoid and/or one or more glucocorticoid comprises a pH from 6 to 8. The pH may comprise from 6 to 7.5.

In one embodiment of any above form, the one or more mineralocorticoid and/or one or more glucocorticoid comprises a balanced salt solution. The balanced salt solution may comprise a saline and a buffer. The balanced salt solution one or more of sodium chloride; potassium chloride; calcium chloride (dehydrate); magnesium chloride (hexahydrate); sodium acetate (trihydrate); sodium citrate (dehydrate); hydrochloric acid; sodium hydroxide and water for injection.

According to any one of the above forms, the one or more mineralocorticoid and/or one or more glucocorticoid of the invention may comprise a sustained release composition.

In a particular embodiment of any one of the above forms, the one or more mineralocorticoid and/or one or more glucocorticoid may be sterilized.

In one embodiment of any one of the above forms, the method further comprises administering to the subject at least one additional agent.

The at least one additional agent may comprise an anti-VEGF (anti-Vascular Endothelial Growth Factor). The anti-VEGF may comprise one or more of ranibizumab (brand name Lucentis®); aflibercept (brand name Eylea®); bevacizumab (brand name Avastin®) and OPT-302.

According to any one of the above forms, when the one or more change is detected, a treatment with hemp, hemp oil or a pharmaceutically effective extract is applied.

In one embodiment of any one of the above forms, the hemp, hemp oil or pharmaceutically effective extract thereof comprises a cannabinoid. The cannabinoid may comprise cannabidiol.

In another embodiment of any one of the above forms, the hemp, hemp oil or pharmaceutically active extract thereof may comprise a low Tetrahydrocannabinol (THC) hemp, hemp oil or pharmaceutically effective extract thereof.

In another embodiment of any one of the above form, the hemp, hemp oil or pharmaceutically effective extract may comprise a *Cannabis Ruderalis.*

In yet another embodiment of any one of the above forms, the hemp, hemp oil or a pharmaceutically effective extract comprises a water-soluble dosage form.

In another embodiment of any one of the above forms, the hemp oil is obtained from hemp seeds.

In another embodiment of any one of the above forms, the hemp oil is cold-pressed.

In another embodiment of any one of the above forms, the hemp oil comprises about 80% to 90% balanced Omega fatty acids. That is, hemp oil comprises Omega 3, (ALA), Omega 6 (LA), Omega 6 (GLA), and Omega 9 (oleic acid), which in combination may amount to 80% to 90% of the composition of the hemp oil.

The hemp oil may comprise about 88% balanced Omega fatty acids. That is, the hemp oil may comprise about 88 g Omega fatty acids per 100 g of hemp oil.

The hemp oil may comprise about 15% to 25% Omega 3, (ALA), about 50% to 60% Omega 6 (LA), about 1% to 5% Omega 6 (GLA), and about 10% to 15% Omega 9 (oleic acid), per 100 g of hemp oil.

The hemp oil may comprise about 1 g to 5 g Omega 3, (ALA), about 5 g to 15 g Omega 6 (LA), about 0.2 g to 1 g Omega 6 (GLA), and about 1 g to 5 g Omega 9 (oleic acid), per 20 g of hemp oil.

In some embodiments of any one of the above forms, the hemp oil may comprise about 3.5 g Omega 3, (ALA), about 11.2 g Omega 6 (LA), about 0.4 g Omega 6 (GLA), and about 2.5 g Omega 9 (oleic acid).

In some embodiments of any one of the above forms, the hemp oil may comprise about 3.3 g Omega 3, (ALA), about 10.7 g Omega 6 (LA), about 0.7 g Omega 6 (GLA), and about 2.7 g Omega 9 (oleic acid).

In another embodiment of any one of the above forms, the hemp oil may have a ratio of Omega 3 to Omega 6 of between about 1:5.2 and 5:16. The hemp oil may have a ratio of Omega 3 to Omega 6 of about 3.5:11.6. The hemp oil may comprise a 1:3 ratio of omega 3 and 6.

In another embodiment of any one of the above forms, the hemp, hemp oil or a pharmaceutically effective extract is for use or when used as a carrier or delivery vehicle for one or more compounds. The one or more compounds may be pharmaceutically active. The one or more compounds may comprise an hydrophobic compound.

In still another embodiment, the hemp, hemp oil; or pharmaceutically effective extract comprises a form suitable for administration by one or more of intradermal, intramuscular, intraperitoneal, parenteral, intravenous, subcutaneous, intranasal, epidural, sublingual, intracerebral, intravaginal, transdermal (e.g., via a patch), rectal, by inhalation, transmucosal, or topical, particularly to the ears, nose, eyes, or skin. The pharmaceutical composition may be injectable. The parenteral or injectable form may comprise any suitable form for parenteral or injectable administration such as an injectable solution, an injectable suspension, an injectable emulsion, and an injection in a form that is prepared at the time of use. Formulations for parenteral administration may be in a configuration such as an aqueous or nonaqueous isotonic aseptic solution or suspension. The injectable form may be for intravitreal injection.

In another particular embodiment of any above form, the hemp, hemp oil or a pharmaceutically effective extract is preservative free.

In another particular embodiment of any above form, the hemp, hemp oil or a pharmaceutically effective extract is prophylactic.

In a particular embodiment of any one of the above forms, the hemp, hemp oil or a pharmaceutically effective extract is sterilized.

In another embodiment of any above form, the hemp, hemp oil or a pharmaceutically effective extract functions as a carrier for one or more compounds.

As used herein, except where the context requires otherwise, the term "comprise" and variations of the term, such as "comprising", "comprises" and "comprised", are not intended to exclude further additives, components, integers or steps.

Further forms and/or features of the present invention will become apparent from the following detailed description.

BRIEF DESCRIPTION OF THE DRAWINGS

In order that the invention may be readily understood and put into practical effect, reference will now be made to embodiments of the present invention with reference to the accompanying drawings, wherein like reference numbers refer to identical elements. The drawings are provided by way of example only, wherein:

FIG. 1B(ii), in the provisional application AU2020904628 this figure was a grayscale version of FIG. 1B(i), which was provided in colour. The provisional application is referred to herein and both figures are retained for consistency.

FIGS. 1C and 1D(i) are a retinal angiogram and a fundus image, respectively, of the same eye shown in FIG. 1A taken two months later. Note the additional fresh intra-retinal (I) and sub-retinal (S) haemorrhages as well as pigment clumping at and above the macula. While shown without colour here, please refer to provisional application AU2020904628 for a colour version of FIG. 1D(i).

FIG. 1D(ii), in the provisional application AU2020904628, this figure was a grayscale version of FIG. 1D(i), which was provided in colour. The provisional application is referred to herein and both figures are retained for consistency.

FIG. 1F(ii), in the provisional application AU2020904628, this figure was a grayscale version of FIG. 1F(i), which was provided in colour. The provisional application is referred to herein and both figures are retained for consistency.

FIG. 2A(ii), in the provisional application AU2020904628, this figure was a grayscale version of FIG. 2A(i), which was provided in colour. The provisional application is referred to herein and both figures are retained for consistency.

FIG. 2B(ii), in the provisional application AU2020904628, this figure was a grayscale version of FIG. 2B(i), which was provided in colour. The provisional application is referred to herein and both figures are retained for consistency.

FIG. 5A(ii) and FIG. 5B(ii) are grayscale versions of FIGS. 5A(i) and 5B(i), respectively.

Figure 1A:
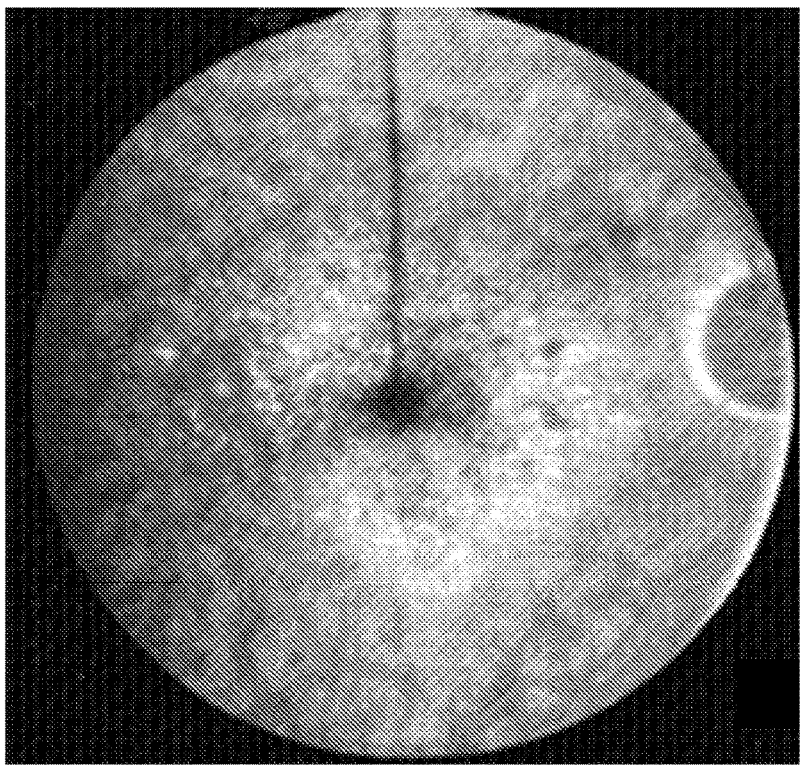
FIG. 1A is a retinal angiogram showing a right eye with mottled fundus and disturbed RPE. A detachment of the macula had been suspected but was not shown on angiography.

Skilled addressees will appreciate that elements in the drawings are illustrated for simplicity and clarity and have not necessarily been drawn to scale. For example, the relative dimensions of some elements in the drawings may be distorted to help improve understanding of embodiments of the present invention.

DETAILED DESCRIPTION OF THE INVENTION

The present invention relates to a method of detecting one or more change in an eye. More particularly, this invention relates to a method of detecting one or more change in an eye and providing a diagnosis, indication or prognosis of an eye disease or eye condition or a predisposition thereto.

The macula is an oval-shaped pigmented area near the centre of the retina. The macula in humans has a diameter of around 5.5 mm and is subdivided into the umbo, foveola, foveal avascular zone, fovea, parafovea, and perifovea areas.

The retinal pigmented epithelium (RPE) is the pigmented cell layer just outside the neurosensory retina that nourishes retinal visual cells. The RPE is attached to the underlying choroid and overlying retinal visual cells. The RPE is composed of a single layer of hexagonal cells that are densely packed with pigment granules.

The macula region of the retina includes a corresponding region of RPE.

In a broad form, the invention is directed to a method in which an image, such as one or more high resolution digital image is used to detect changes in the retina over time. The one or more high resolution digital images allow the detection of slight changes in for example, the pigment in the RPE, which the inventor hypothesises indicates neovascularization. While not wanting to be bound by any one theory, the inventor further hypothesises that the detected slight changes in pigment are not likely to be penetrative at the earliest stages of detection by this modality. Significantly, these changes may not be observable with the naked eye. The inventor has made the unexpected discovery that with high resolution imaging, these changes can be observed.

Advantageously, by using the inventor's discovery, and by monitoring a patient, the change can be detected earlier than it is currently.

As will be shown below, the inventor's studies have shown new vessel formation is observable with retinal imaging techniques such as, OCT, fundus imaging and histological data.

In one embodiment, the invention provides a method of detecting one or more change in an eye such as, a darkening or lightening in pigment of the Retinal Pigmented Epithelium (RPE) and/or macula. The darkening or lightening may comprise one or both of a pigmentary disturbance and mottling. The change may be in absence of drusen or any change in drusen.

The change may be an increase or decrease in the pigment in an area of the RPE. That is one area may increase pigmentation and neighbouring area may decrease pigmentation across any two points in time. The change may occur in either direction, that is one area may increase pigmentation from one time point to another time point or may decrease pigmentation for that time-shift while a neighbouring or other area may decrease pigmentation for the same time-shift. An area that has previously had an increase in pigmentation may later have a decrease in pigmentation. An area that has previously had a decrease in pigmentation may later have an increase in pigmentation.

While not wanting to be bound by any one theory, this inventor hypothesises that this disorganisation of the RPE is due to the cleavage of the RPE from the Bruch's membrane by the neovascularisation. This detection is conducted in the absence of drusen.

The method comprises comparing an image of the eye with at least one asynchronous image of the eye to thereby detect the one or more change in the eye.

The invention also provides a method of diagnosing or providing an indication of an eye disease or eye condition or a predisposition thereto or a neurodegenerative disease or condition or a predisposition thereto. The method comprising comparing an image of the eye with at least one asynchronous image of the eye to detect the one or more change in the eye and when a change is detected providing a diagnosis of, indication of or predisposition to an eye disease or eye condition or a neurodegenerative disease or condition or a predisposition thereto.

The change may comprise a change in pigment of the Retinal Pigmented Epithelium (RPE). The change in pigment may indicate neovascularization or a new blood vessel. The detected change in pigment may not be penetrative.

The image and the asynchronous image comprise digital images.

The one or more asynchronous image may be asynchronous by one day, one week, one fortnight, one month, one quarter, one half-year or one year.

The comparing may be by one or more processing element. The processing element may comprise an electronic circuit, a microprocessor or an internal component of a microprocessor.

The comparing may be by an artificial intelligence such as, a neural network or artificial neural network, which may be in the form of a convolutional neural network; a deep neutral network or a deep convolutional neural network. The search may be of an entire image. When the neural network is a convolutional neural network it may be an INCEPTION-RESNET-V2 network or a network based thereon.

To detect the change, the neural network may comprise an object detection system. The object detection system may use a neural network based YOLO (you only look once) real time object detection architecture.

The neural network may comprise an image classifier which may comprise a neural network based on VGG (Visual Geometry Group) classifier. The classifier may receive the one or more digital image. The classifier may be pre-trained. The pre-training may comprise training on a data set. The output model of the network may be modified to identify only two classes: received digital images containing a detected change, i.e. positive, and received digital images not containing a detected change, i.e. negative. The classifier may have been trained by fine tuning on a training set of example images. The example images may comprise, more than one hundred, more than one thousand, more than a hundred thousand, or more than one million example digital images. The training set may comprise positive and negative labelled images. When the digital image is fed into the classifier network, the analysis may determine as output a confidence that the image is positive for the detected change. The determined confidence may comprise for example a confidence output of 0% which is very unlikely to show a detected change and a confidence output of 100% which is very likely to show a detected change. A threshold may be used to limit which images are deemed positive and which are deemed negative. The threshold may comprise a threshold value which may be dynamically adjusted so that a top margin of images are deemed positive and sent on for manual review. The top margin may comprise a top 5; 10; 15; 20; or 25% of received cropped images with respected to determined confidence.

The comparison may comprise a real time object detector. The real time object detector may identify the one or more change. The comparison may comprise a positive identification of the one or more change. The real time object detector may output a location of the detected one or more change in the digital image and optionally a confidence score the one or more change has been detected.

The comparing may comprise image registration. The image registration may comprise transforming the image and the at least one asynchronous image into one coordinate system.

The image and the at least one asynchronous image may be processed. The processing may include removing noise.

The comparing may comprise one or more of determining intensity levels; determining a distribution of gradient magnitude; determining intensity profile.

The change may be detected by comparing intensity levels. The change may be detected in one or more of the retina and the macula.

The methods of the invention may also include image pre-processing such as, colour channel extraction, median filtering and/or Gaussian smoothing.

The image and the at least one asynchronous image comprise one or more 2-D image and/or one or more 3-D image. The one or more 2-D image may comprise a fundus images or an Optical Coherence Tomography (OCT) image. The one or more 3-D image may comprise one or more OCT image.

In another aspect, the inventor has applied the knowledge that what happens in one eye always, or often, occurs in the other, or fellow eye. Accordingly, the fellow eye can be used to confirm or for validation of the method of the invention. The method can be used in the fellow eye of a patient who has a diseased eye, in order to test the detection methodology.

In this manner, the invention is at least partly predicated on the inventors' unexpected discovery that monitoring the fellow eye of a person who has neovascularisation in one retina can confirm disease or condition progression.

The change may be detected using an algorithm or methodology trained on one or more fellow eye of a subject with neovascularisation in the other retina. The training may be with the method, computer program product, device or system according to any one of the above forms.

Significantly, the temporal changes detected with the method of the invention can also be used to diagnose, detect or indicate a likelihood of developing Alzheimer's disease. While not wanting to be bound by any one theory, the inventor hypothesises that colour changes in digital photographs may be indicative, prognostic or diagnostic of Alzheimer's disease or another neurodegenerative disease or condition such as, Parkinson's disease; Huntington's disease; Amyotrophic lateral sclerosis; and Batten disease. The neurodegenerative disease or condition may also comprise an encephalopathy such as, a transmissible spongiform encephalopathy.

In one example, an in vivo dye can be utilised to visualise inflammatory changes in the retina that allows diagnosis or an indication of Alzheimer's disease or another neurodegenerative disease or condition.

The visualised change may be a change in colour or intensity. Without wanting to be bound by any one theory, the inventor hypothesises that in association with these neurodegenerative diseases and conditions, retinal vessels became intense for markers of MHC class II proteins. In a study of thirty patients who died from Alzheimer's Disease, in a majority of the subjects there was an upregulation of MHC class II antigens. Without wanting to be bound by any one theory, the inventor hypothesises that an assay to visualise or otherwise detect fluorescent tags for MHC or class II antigens or other inflammatory markers may diagnostic, prognostic or indicative of a neurodegenerative disease or condition.

The high resolution imaging may be fundus photography, OCT or another imaging modality.

The subject may be middle aged or older. Images may be collected from age 40, 45, 50, 55, 60, 65 or older.

The eye condition may comprise any eye condition such as, early or sub-clinical stages of an eye disease.

Advantageously, the present invention may be implemented with existing instrumentation and in the context of existing physical examination. Fundus photography and OCT imaging is becoming more common and typically, from age of 60 onwards, everyone's eyes are imaged annually. If these images are combined with the present invention AMD can be detected much earlier and possibly prevented in some or many cases.

As used herein, the term "eye condition" includes any eye condition such as, early or sub-clinical stages of an eye disease.

As used herein, the term "eye disease" includes any eye disease such as, macular degeneration, maculopathy including an age related maculopathy (ARM), age related macular degeneration (AMD) including both the dry (geographic atrophy) and wet (choroidal neovascularisation (CNV)), an exudative eye disease or condition, retinal pigment epithelium detachments (PED), forms of age related macular degeneration, a diabetic eye disease or condition including a diabetic retinopathy and diabetic macular oedema (DME), corneal neovascularisation, cyclitis, Hippel-Lindel disease, retinopathy of prematurity (also known as retrolental fibroplasia), pterygium, histoplasmosis, iris neovascularisation, glaucoma, glaucoma-associated neovascularisation, Purtcher's retinopathy, ocular hypertension, macular oedema, Coats' disease, uveitis including anterior uveitis, Sicca syndrome, hereditary diseases associated with increased extra-intracellular lipid storage/accumulation, juvenile macular degeneration, an ocular allergy and an ocular tumour. The ocular tumour may comprise a retinoblastoma and/or a melanoma.

The eye disease or condition may comprise a back of eye disease or conditions including an exudative back of eye exudative disease or condition. The back of eye disease or condition may comprise an eye disease or condition involving the retina, macular and/or fovea in the posterior region of the eye. Examples of back of eye disease include macular oedema, such as clinical macular oedema or angiographic cystoid macular oedema arising from various aetiologies, such as diabetes, exudative macular degeneration and macula oedema arising from laser treatment of the retina, retinal ischemia and choroidal neovascularisation, a retinal disease, an inflammatory disease, uveitis associated with neoplasms, such as retinoblastoma or psuedoglioma, neovascularisation following vitrectomy, a vascular disease and neovascularisation of the optic nerve. The retinal disease may be one or more of diabetic retinopathy, diabetic retinal oedema, retinal detachment, senile macular degeneration due to sub-retinal neovascularisation and myopic retinopathy. The vascular disease may be one or more of retinal ischemia, choroidal vascular insufficiency, choroidal thrombosis and neovascular retinopathies resulting from carotid artery ischemia.

The invention may find application to an exudative eye disease and/or condition, a back of the eye exudative eye disease and/or condition, age-related macular degeneration, wet age related macular degeneration, a diabetic macular oedema (DME), cystoid macular oedema (CMO); maculopathy; and/or an ocular tumour. The ocular tumour may comprise a retinoblastoma and/or a melanoma. The eye disease and/or condition may be a diabetic eye disease and/or condition. Other eye disease and/conditions include (non-infectious) conjunctivitis, anterior uveitis and an ocular allergy.

The invention has particular application to age related macular degeneration (AMD) and wet AMD.

The invention further has particular application to dry AMD. Dry AMD may comprise early AMD and geographic atrophy (GA), distinct from exudative AMD. Distinct from exudative AMD means exudative AMD is not comprised within dry AMD.

In another embodiment, treatment comprises prophylactic treatment. The prophylactic treatment may comprise treatment to prevent dry AMD, treatment of a predisposition to dry AMD or treatment of a susceptibility to dry AMD. The predisposition or susceptibility may comprise an individual with a family history of an eye disease or condition such as, dry AMD. Prevention or prophylaxis may be successful if the development of dry AMD is completely or partially prevented or slowed down.

The eye disease and/or condition may be an exudative eye disease and/or condition. The eye disease and/or condition may be a back of the eye exudative eye disease and/or condition.

The eye disease and/or condition may be a diabetic macular oedema (DME), cystoid macular oedema (CMO); maculopathy; and/or an ocular tumour.

The one or more eye disease or condition may comprises glaucoma.

The eye disease and/or condition may be a diabetic eye disease and/or condition.

Other eye disease and/conditions include (non-infectious) conjunctivitis, anterior uveitis and an ocular allergy.

"Prevention" or "prophylaxis," as used herein, refers to prophylactic or preventative measures. Those in need of prevention or prophylaxis include those in whom the eye disease or condition is to be prevented, and in some embodiments, may be predisposed or susceptible to the eye disease or condition e.g. individuals with a family history of an eye disease or condition.

The terms "subject", "patient" or "individual," which are used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including humans, as well as non-human primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In specific embodiments, the "subject", "patient" or "individual" is a human in need of treatment or prophylaxis of an eye disease or condition, including in subjects with a diabetic eye disease or condition or an ocular tumour. In specific embodiments, the terms "subject", "patient" or "individual" refer to any single human subject, including a patient, eligible for treatment who is experiencing or has experienced one or more signs, symptoms, or other indicators of an eye disease or condition or predisposition thereto, whether, for example, newly diagnosed or previously diagnosed and now experiencing a recurrence or relapse, or is at risk for an eye disease or condition, no matter the cause. Intended to be included as a "subject", "patient" or "individual" are any subjects involved in clinical research trials not showing any clinical sign of disease, or subjects involved in epidemiological studies, or subjects once used as controls. The "subject", "patient" or "individual" may have been previously treated with a medicament for an eye disease or condition, or not so treated.

The invention also provides a computer program product comprising a non-transitory computer useable medium. The computer program product comprises a computer usable medium and computer readable program code embodied on said computer usable medium for detecting one or more change in an eye. The computer readable code comprises computer readable program code devices (i) configured to cause the computer to compare an image of the eye with at least one asynchronous image of the eye to thereby detect the one or more change in the eye.

The invention further provides a computer program product comprising a non-transitory computer useable medium wherein the computer program product comprises a computer usable medium and computer readable program code embodied on said computer usable medium for diagnosing or providing an indication of an eye disease or eye condition or a predisposition thereto or a neurodegenerative disease or condition or a predisposition thereto. The computer readable code comprises computer readable program code devices (i) configured to cause the computer to compare an image of the eye with at least one asynchronous image of the eye to thereby detect the one or more change in the eye. The code also comprises computer readable program code devices (ii) configured, when a change is detected, to cause the computer to provide a diagnosis of, indication of or prognosis of an eye disease or eye condition or a neurodegenerative disease or condition or a predisposition thereto.

The invention also provides a device and a system for detecting these changes and a device for diagnosing, indicating or providing a prognosis of an eye disease or eye condition or a predisposition thereto or a neurodegenerative disease or condition or a predisposition thereto.

Figure 6A:
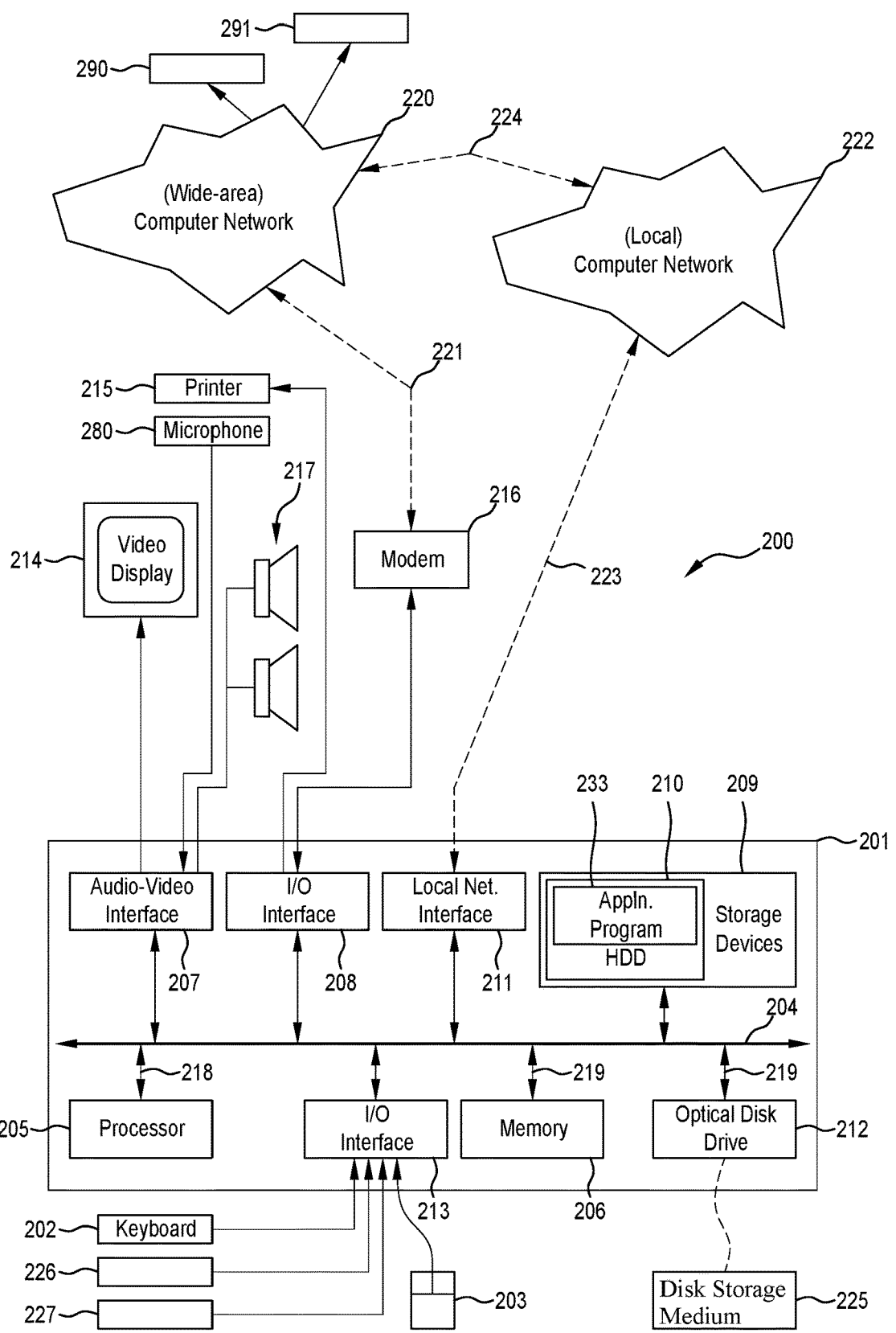
FIGS. 6A and 6B illustrate a computer system for use according to one embodiment of the invention.
Figure 6B:
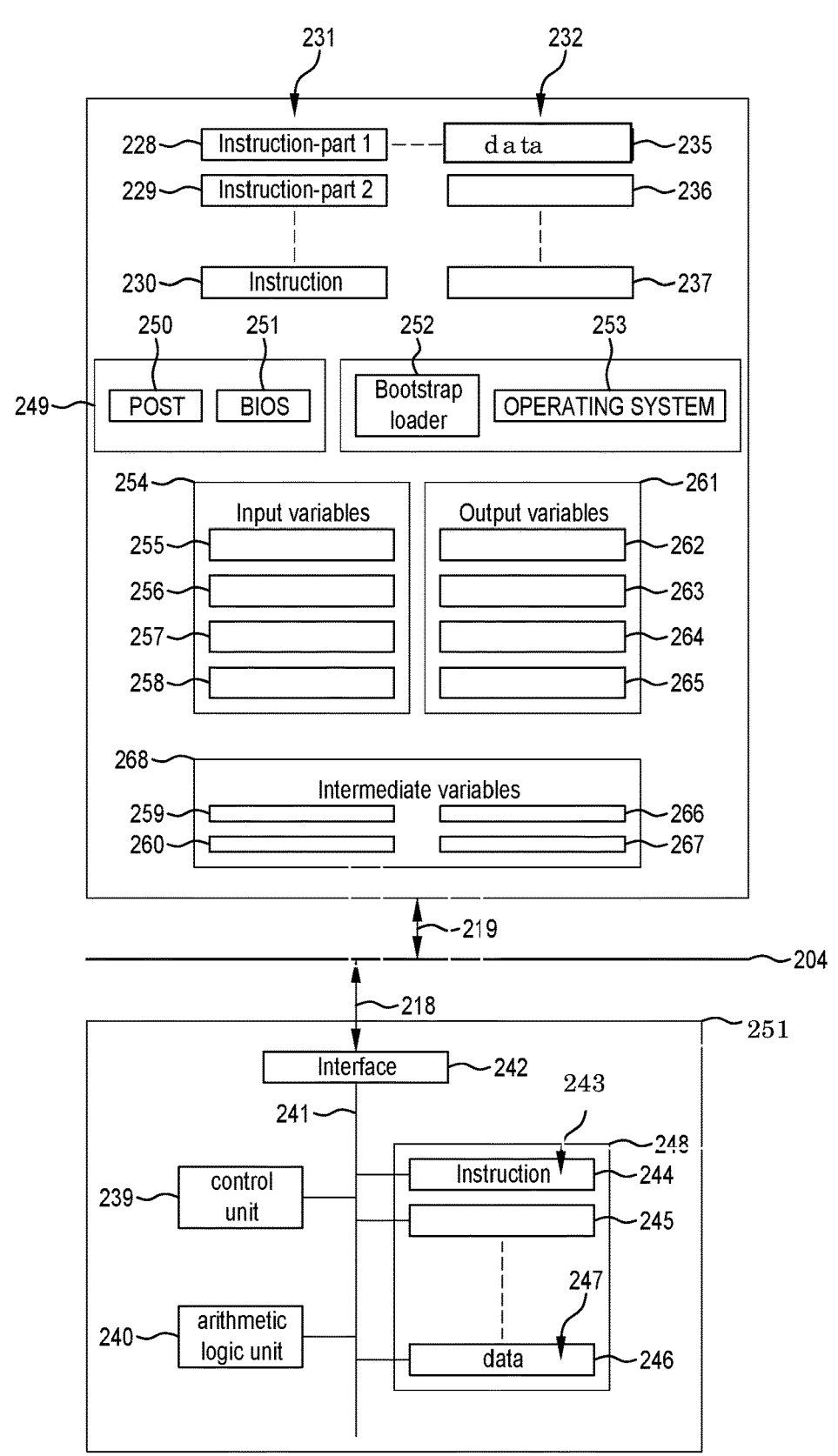

One embodiment of a computing device 200 suitable for use in the present invention is shown in FIGS. 6A and 6B. In the embodiment shown, computing device 200 comprises a computer module 201 comprising input devices such as a keyboard 202, a mouse pointer device 203, a scanner 226, an external hard drive 227, and a microphone 280; and output devices including a printer 215, a display device 214 and loudspeakers 217. In some embodiments video display 214 may comprise a touchscreen.

A Modulator-Demodulator (Modem) transceiver device 216 may be used by the computer module 201 for communicating to and from a communications network 220 via a connection 221. The network 220 may be a wide-area network (WAN), such as the Internet, a cellular telecommunications network, or a private WAN. Through the network 220, computer module 201 may be connected to other similar personal devices 290 or server computers 291. Where the connection 221 is a telephone line, the modem 216 may be a traditional "dial-up" modem. Alternatively, where the connection 221 is a high capacity (e.g.: cable) connection, the modem 216 may be a broadband modem. A wireless modem may also be used for wireless connection to network 220.

The computer module 201 typically includes at least one processing element, shown in the form of a microprocessor 205, and a memory 206 for example formed from semiconductor random access memory (RAM) and semiconductor read only memory (ROM). The module 201 also includes a number of input/output (I/O) interfaces including: an audio-video interface 207 that couples to the video display 214, loudspeakers 217 and microphone 280; an I/O interface 213 for the keyboard 202, mouse 203, scanner 226 and external hard drive 227; and an interface 208 for the external modem 216 and printer 215. In some implementations, modem 216 may be incorporated within the computer module 201, for example within the interface 208. The computer module 201 also has a local network interface 211 which, via a connection 223, permits coupling of the computing device 200 to a local computer network 222, known as a Local Area Network (LAN).

As also illustrated, the local network 222 may also couple to the wide network 220 via a connection 224, which would typically include a so-called "firewall" device or device of similar functionality. The interface 211 may be formed by an Ethernet circuit card, a Bluetooth wireless arrangement or an IEEE 802.11 wireless arrangement or other suitable interface.

The I/O interfaces 208 and 213 may afford either or both of serial and parallel connectivity, the former typically being implemented according to the Universal Serial Bus (USB) standards and having corresponding USB connectors (not illustrated).

Storage devices 209 are provided and typically include a hard disk drive (HDD) 210. Other storage devices such as, an external HD 227, a disk drive (not shown) and a magnetic tape drive (not shown) may also be used. An optical disk drive 212 is typically provided to act as a non-volatile source of data. Portable memory devices, such as optical disks (e.g.: CD-ROM, DVD, Blu-Ray Disc), USB-RAM, external hard drives and floppy disks for example, may be used as appropriate sources of data to the computing device 200. Another source of data to computing device 200 is provided by the at least one server computer 291 through network 220.

The components 205 to 213 of the computer module 201 typically communicate via an interconnected bus 204 in a manner that results in a conventional mode of operation of computing device 200. In the embodiment shown in FIGS. 6A and 6B, processor 205 is coupled to system bus 204 through connections 218. Similarly, memory 206 and optical disk drive 212 are coupled to the system bus 204 by connections 219. Examples of computing devices 200 on which the described arrangements can be practiced include IBM-PC's and compatibles, Sun Sparc stations, Apple computers; smart phones; tablet computers or like a device comprising a computer module like computer module 201. It is to be understood that when computing device 200 comprises a smart phone or a tablet computer, display device 214 may comprise a touchscreen and other input and output devices may not be included such as, mouse pointer device 201; keyboard 202; scanner 226; and printer 215.

FIG. 6B is a detailed schematic block diagram of microprocessor 205 and a memory 234. The memory 234 represents a logical aggregation of all the memory modules, including the storage device 209 and semiconductor memory 206, which can be accessed by the computer module 201 in FIG. 6A.

The methods of the invention may be implemented using computing device 200 wherein the methods may be implemented as one or more software application programs 233 executable within computer module 201. In particular, the steps of the methods of the invention may be effected by instructions 231 in the software carried out within computer module 201

The software instructions 231 may be formed as one or more code modules, each for performing one or more particular tasks. The software 233 may also be divided into two separate parts, in which a first part and the corresponding code modules performs the method of the invention and a second part and the corresponding code modules manage a graphical user interface between the first part and the user.

The software 233 may be stored in a computer readable medium, including in a storage device of a type described herein. The software is loaded into the computing device 200 from the computer readable medium or through network 221 or 223, and then executed by computing device 200. In one example the software 233 is stored on storage medium 225 that is read by optical disk drive 212. Software 233 is typically stored in the HDD 210 or the memory 206.

A computer readable medium having such software 233 or computer program recorded on it is a computer program product. The use of the computer program product in the computing device 200 preferably effects a device or apparatus for implementing the methods of the invention.

In some instances, the software application programs 233 may be supplied to the user encoded on one or more disk storage medium 225 such as a CD-ROM, DVD or Blu-Ray disc, and read via the corresponding drive 212, or alternatively may be read by the user from the networks 220 or 222. Still further, the software can also be loaded into the computing device 200 from other computer readable media. Computer readable storage media refers to any non-transitory tangible storage medium that provides recorded instructions and/or data to the computer module 201 or computing device 200 for execution and/or processing. Examples of such storage media include floppy disks, magnetic tape, CD-ROM, DVD, Blu-ray Disc, a hard disk drive, a ROM or integrated circuit, USB memory, a magneto-optical disk, or a computer readable card such as a PCMCIA card and the like, whether or not such devices are internal or external of the computer module 201. Examples of transitory or non-tangible computer readable transmission media that may also participate in the provision of software application programs 233, instructions 231 and/or data to the computer module 201 include radio or infra-red transmission channels as well as a network connection 221, 223, 334, to another computer or networked device 290, 291 and the Internet or an Intranet including email transmissions and information recorded on Websites and the like.

The second part of the application programs 233 and the corresponding code modules mentioned above may be executed to implement one or more graphical user interfaces (GUIs) to be rendered or otherwise represented upon display 214. Through manipulation of, typically, keyboard 202, mouse 203 and/or screen 214 when comprising a touchscreen, a user of computing device 200 and the methods of the invention may manipulate the interface in a functionally adaptable manner to provide controlling commands and/or input to the applications associated with the GUI(s). Other forms of functionally adaptable user interfaces may also be implemented, such as an audio interface utilizing speech prompts output via loudspeakers 217 and user voice commands input via microphone 280. The manipulations including mouse clicks, screen touches, speech prompts and/or user voice commands may be transmitted via network 220 or 222.

When the computer module 201 is initially powered up, a power-on self-test (POST) program 250 may execute. The POST program 250 is typically stored in a ROM 249 of the semiconductor memory 206. A hardware device such as the ROM 249 is sometimes referred to as firmware. The POST program 250 examines hardware within the computer module 201 to ensure proper functioning, and typically checks processor 205, memory 234 (209, 206), and a basic input-output systems software (BIOS) module 251, also typically stored in ROM 249, for correct operation. Once the POST program 250 has run successfully, BIOS 251 activates hard disk drive 210. Activation of hard disk drive 210 causes a bootstrap loader program 252 that is resident on hard disk drive 210 to execute via processor 205. This loads an operating system 253 into RAM memory 206 upon which operating system 253 commences operation. Operating system 253 is a system level application, executable by processor 205, to fulfil various high level functions, including processor management, memory management, device management, storage management, software application interface, and generic user interface.

Operating system 253 manages memory 234 (209, 206) in order to ensure that each process or application running on computer module 201 has sufficient memory in which to execute without colliding with memory allocated to another process. Furthermore, the different types of memory available in the computing device 200 must be used properly so that each process can run effectively. Accordingly, the aggregated memory 234 is not intended to illustrate how particular segments of memory are allocated, but rather to provide a general view of the memory accessible by computer module 201 and how such is used.

Processor 205 includes a number of functional modules including a control unit 239, an arithmetic logic unit (ALU) 240, and a local or internal memory 248, sometimes called a cache memory. The cache memory 248 typically includes a number of storage registers 244, 245, 246 in a register section storing data 247. One or more internal busses 241 functionally interconnect these functional modules. The processor 205 typically also has one or more interfaces 242 for communicating with external devices via the system bus 204, using a connection 218. The memory 234 is connected to the bus 204 by connection 219.

Application program 233 includes a sequence of instructions 231 that may include conditional branch and loop instructions. Program 233 may also include data 232 which is used in execution of the program 233. The instructions 231 and the data 232 are stored in memory locations 228, 229, 230 and 235, 236, 237, respectively. Depending upon the relative size of the instructions 231 and the memory locations 228-230, a particular instruction may be stored in a single memory location as depicted by the instruction shown in the memory location 230. Alternately, an instruction may be segmented into a number of parts each of which is stored in a separate memory location, as depicted by the instruction segments shown in the memory locations 228 and 229.

In general, processor 205 is given a set of instructions 243 which are executed therein. The processor 205 then waits for a subsequent input, to which processor 205 reacts by executing another set of instructions. Each input may be provided from one or more of a number of sources, including data generated by one or more of the input devices 202, 203, or 214 when comprising a touchscreen, data received from an external source across one of the networks 220, 222, data retrieved from one of the storage devices 206, 209 or data retrieved from a storage medium 225 inserted into the corresponding reader 212. The execution of a set of the instructions may in some cases result in output of data. Execution may also involve storing data or variables to the memory 234.

The disclosed arrangements use input variables 254 that are stored in the memory 234 in corresponding memory locations 255, 256, 257, 258. The described arrangements produce output variables 261 that are stored in the memory 234 in corresponding memory locations 262, 263, 264, 265. Intermediate variables 268 may be stored in memory locations 259, 260, 266 and 267.

The register section 244, 245, 246, the arithmetic logic unit (ALU) 240, and the control unit 239 of the processor 205 work together to perform sequences of micro-operations needed to perform "fetch, decode, and execute" cycles for every instruction in the instruction set making up the program 233. Each fetch, decode, and execute cycle comprises:

(a) a fetch operation, which fetches or reads an instruction 231 from memory location 228, 229, 230;

(b) a decode operation in which control unit 239 determines which instruction has been fetched; and (c) an execute operation in which the control unit 239 and/or the ALU 240 execute the instruction.

Thereafter, a further fetch, decode, and execute cycle for the next instruction may be executed. Similarly, a store cycle may be performed by which the control unit 239 stores or writes a value to a memory location 232.

Each step or sub-process in the methods of the invention may be associated with one or more segments of the program 233, and may be performed by register section 244-246, the ALU 240, and the control unit 239 in the processor 205 working together to perform the fetch, decode, and execute cycles for every instruction in the instruction set for the noted segments of program 233.

One or more other computers 290 may be connected to the communications network 220 as seen in FIG. 6A. Each such computer 290 may have a similar configuration to the computer module 201 and corresponding peripherals.

One or more other server computer 291 may be connected to the communications network 220. These server computers 291 response to requests from the personal device or other server computers to provide information.

The methods of the invention may alternatively be implemented in dedicated hardware such as one or more integrated circuits performing the functions or sub functions of the described methods. Such dedicated hardware may include graphic processors, digital signal processors, or one or more microprocessors and associated memories.

The invention also allows telemedicine, along with the transfer between distant sites of patient medical records, medical images and output data from medical devices. Additionally, the one or more image of the eye and one or more asynchronous image may be communicated to a remote location by the network to allow remote assessment using the methods, devices and system of the invention.

When the one or more change is detected, one or more mineralocorticoid and/or one or more glucocorticoid or a therapeutically active analogue, derivative, homolog, pharmaceutically acceptable salt or conjugate thereof may be applied to the eye.

The one or more mineralocorticoid or a therapeutically active analogue, derivative, homolog, pharmaceutically acceptable salt or conjugate thereof may comprise one or more of: 11-desoxycortisone (11-DC); fludrocortisone; fludrocortisone acetate (FA); fludrocortisone acetonide; Deoxycorticosterone acetate (DA); Deoxycorticosterone (DS); or Aldosterone; or a therapeutically active analogue, derivative, homolog, pharmaceutically acceptable salt or conjugate thereof.

The one or more glucocorticoid or a therapeutically active analogue, derivative, homolog, pharmaceutically acceptable salt or conjugate thereof may comprise one or more of: cortisol, cortisone, prednisone, prednisolone, methylprednisolone, dexamethasone, betamethasone, triamcinolone, triamcinolone acetonide, beclometasone or a therapeutically active analogue, derivative, homolog, pharmaceutically acceptable salt or conjugate thereof.

The one or more mineralocorticoid and/or more glucocorticoid or a therapeutically active analogue, derivative, homolog, pharmaceutically acceptable salt or conjugate thereof may comprise one or more dual action compounds, wherein each dual action compound is capable of modulating the activity of both a mineralocorticoid receptor and a glucocorticoid receptor.

The dual action compound may comprise one or more of triamcinolone; triamcinolone acetonide; cortisol; cortisone; prednisone; prednisolone; methylprednisolone; fludrocortisone; fludrocortisone acetate; fludrocortisone acetonide; or a therapeutically active analogue, derivative, homolog, pharmaceutically acceptable salt or conjugate thereof.

The one or more mineralocorticoid or one or more glucocorticoid or a therapeutically active analogue, derivative, homolog, pharmaceutically acceptable salt or conjugate thereof may comprise fludrocortisone or a therapeutically active analogue, derivative, homolog, pharmaceutically acceptable salt or conjugate thereof. The therapeutically active analogue, derivative, homolog, pharmaceutically acceptable salt or conjugate thereof may comprise one or more of fludrocortisone acetate and fludrocortisone acetonide.

The one or more mineralocorticoid and/or one or more glucocorticoid or a therapeutically active analogue, derivative, homolog, pharmaceutically acceptable salt or conjugate thereof may comprise triamcinolone acetonide or a therapeutically active analogue, derivative, homolog, pharmaceutically acceptable salt or conjugate thereof.

When the one or more mineralocorticoid and/or one or more glucocorticoid or a therapeutically active analogue, derivative, homolog, pharmaceutically acceptable salt or conjugate thereof comprises triamcinolone acetonide the concentration may comprise 3.0 to 5.0 mg/ml. In one particular embodiment the concentration may comprise 4.0 mg/ml.

In another particular embodiment, the one or more mineralocorticoid and or one or more glucocorticoid or a therapeutically active analogue, derivative, homolog, pharmaceutically acceptable salt or conjugate thereof comprises triamcinolone and fludrocortisone or a therapeutically active analogue, derivative, homolog, pharmaceutically acceptable salt or conjugate of either. The therapeutically active analogue, derivative, homolog, pharmaceutically acceptable salt or conjugate thereof may comprise one or more of fludrocortisone acetate and fludrocortisone acetonide and triamcinolone acetonide.

In another embodiment, the one or more mineralocorticoid and/or one or more glucocorticoid or a therapeutically active analogue, derivative, homolog, pharmaceutically acceptable salt or conjugate thereof comprises a mixture of one or more mineralocorticoid or a therapeutically active analogue, derivative, homolog, pharmaceutically acceptable salt or conjugate thereof and one or more glucocorticoid or a therapeutically active analogue, derivative, homolog, pharmaceutically acceptable salt or conjugate thereof. The mixture may comprise: two or more mineralocorticoids or a therapeutically active analogue, derivative, homolog, pharmaceutically acceptable salt or conjugate thereof; two or more glucocorticoids or a therapeutically active analogue, derivative, homolog, pharmaceutically acceptable salt or conjugate thereof and/or one or more mineralocorticoid or a therapeutically active analogue, derivative, homolog, pharmaceutically acceptable salt or conjugate thereof and one or more glucocorticoids or a therapeutically active analogue, derivative, homolog, pharmaceutically acceptable salt or conjugate thereof.

The one or more mineralocorticoid and/or one or more glucocorticoid may be injected such as, by suprachoroidal injection.

The one or more mineralocorticoid and/or one or more glucocorticoid may be provided in a unit-dose formulation for example in a pre-filled syringe. The pre-filled syringe may comprise two barrels, a first barrel comprising the one or more mineralocorticoid and/or one or more glucocorticoid and a second barrel, different to the first barrel, comprising one or more additional agent.

One or more pharmaceutically acceptable carriers, diluents or excipients may be comprised such as, one or more surfactant or wetting agent.

The surfactant may comprise a polysorbate. The polysorbate may comprise one or more of polysorbate 20 and polysorbate 80. In a particular embodiment the surfactant comprises polysorbate 80.

The pharmaceutically acceptable carrier, diluent or excipient may comprise carboxy methyl cellulose (CMC).

The one or more mineralocorticoid and/or one or more glucocorticoid may further comprise one or more of a pH adjustment composition and water for injection. The pH adjustment composition may comprise hydrochloric acid and/or sodium hydroxide.

The one or more mineralocorticoid and/or one or more glucocorticoid may comprises a pH from 6 to 8. The pH may comprise from 6 to 7.5.

The one or more mineralocorticoid and/or one or more glucocorticoid may comprise a balanced salt solution. The balanced salt solution may comprise a saline and a buffer. The balanced salt solution one or more of sodium chloride; potassium chloride; calcium chloride (dehydrate); magnesium chloride (hexahydrate); sodium acetate (trihydrate); sodium citrate (dehydrate); hydrochloric acid; sodium hydroxide and water for injection.

The one or more mineralocorticoid and/or one or more glucocorticoid is/are preservative free one or more mineralocorticoid and/or one or more glucocorticoid may be preservative free.

The one or more mineralocorticoid and/or one or more glucocorticoid of the invention may comprise a sustained release composition.

The one or more mineralocorticoid and/or one or more glucocorticoid may be sterilized.

At least one additional agent may be administered to the subject. The at least one additional agent may comprise an anti-VEGF (anti-Vascular Endothelial Growth Factor). The anti-VEGF may comprise one or more of ranibizumab (brand name Lucentis®); aflibercept (brand name Eylea®); bevacizumab (brand name Avastin®) and OPT-302.

When the one or more change is detected, a treatment with hemp, hemp oil or a pharmaceutically effective extract may be applied. The hemp, hemp oil or pharmaceutically effective extract thereof may comprise a cannabinoid. The cannabinoid may comprise cannabidiol.

The hemp, hemp oil or pharmaceutically active extract thereof may comprise a low Tetrahydrocannabinol (THC) hemp, hemp oil or pharmaceutically effective extract thereof.

The hemp, hemp oil or pharmaceutically effective extract may comprise a *Cannabis Ruderalis*.

The hemp, hemp oil or a pharmaceutically effective extract may comprise a water-soluble dosage form.

The hemp oil may be obtained from hemp seeds.

The hemp oil may be cold-pressed.

The hemp oil may comprise about 80% to 90% balanced Omega fatty acids. That is, hemp oil comprises Omega 3, (ALA), Omega 6 (LA), Omega 6 (GLA), and Omega 9 (oleic acid), which in combination may amount to 80% to 90% of the composition of the hemp oil.

The hemp oil may comprise about 88% balanced Omega fatty acids. That is, the hemp oil may comprise about 88 g Omega fatty acids per 100 g of hemp oil.

The hemp oil may comprise about 15% to 25% Omega 3, (ALA), about 50% to 60% Omega 6 (LA), about 1% to 5% Omega 6 (GLA), and about 10% to 15% Omega 9 (oleic acid), per 100 g of hemp oil.

The hemp oil may comprise about 1 g to 5 g Omega 3, (ALA), about 5 g to 15 g Omega 6 (LA), about 0.2 g to 1 g Omega 6 (GLA), and about 1 g to 5 g Omega 9 (oleic acid), per 20 g of hemp oil.

The hemp oil may comprise about 3.5 g Omega 3, (ALA), about 11.2 g Omega 6 (LA), about 0.4 g Omega 6 (GLA), and about 2.5 g Omega 9 (oleic acid).

The hemp oil may comprise about 3.3 g Omega 3, (ALA), about 10.7 g Omega 6 (LA), about 0.7 g Omega 6 (GLA), and about 2.7 g Omega 9 (oleic acid).

The hemp oil may have a ratio of Omega 3 to Omega 6 of between about 1:5.2 and 5:16. The hemp oil may have a ratio of Omega 3 to Omega 6 of about 3.5:11.6. The hemp oil may comprise a 1:3 ratio of omega 3 and 6.

The hemp, hemp oil or a pharmaceutically effective extract may be for use or when used as a carrier or delivery vehicle for one or more compounds. The one or more compounds may be pharmaceutically active. The one or more compounds may comprise an hydrophobic compound.

The hemp, hemp oil; or pharmaceutically effective extract may comprise a form suitable for administration by one or more of intradermal, intramuscular, intraperitoneal, parenteral, intravenous, subcutaneous, intranasal, epidural, sublingual, intracerebral, intravaginal, transdermal (e.g., via a patch), rectal, by inhalation, transmucosal, or topical, particularly to the ears, nose, eyes, or skin. The pharmaceutical composition may be injectable. The parenteral or injectable form may comprise any suitable form for parenteral or injectable administration such as an injectable solution, an injectable suspension, an injectable emulsion, and an injection in a form that is prepared at the time of use. Formulations for parenteral administration may be in a configuration such as an aqueous or nonaqueous isotonic aseptic solution or suspension. The injectable form may be for intravitreal injection.

The hemp, hemp oil or a pharmaceutically effective extract may be preservative free.

The hemp, hemp oil or a pharmaceutically effective extract may be prophylactic.

The hemp, hemp oil or a pharmaceutically effective extract may be sterilized.

Advantageously, the hemp, hemp oil or a pharmaceutically effective extract may function as a carrier for one or more compounds.

The following non-limiting examples illustrate the invention. These examples should not be construed as limiting: the examples are included for the purposes of illustration only. The Examples will be understood to represent an exemplification of the invention.

EXAMPLES

Figure 1B:
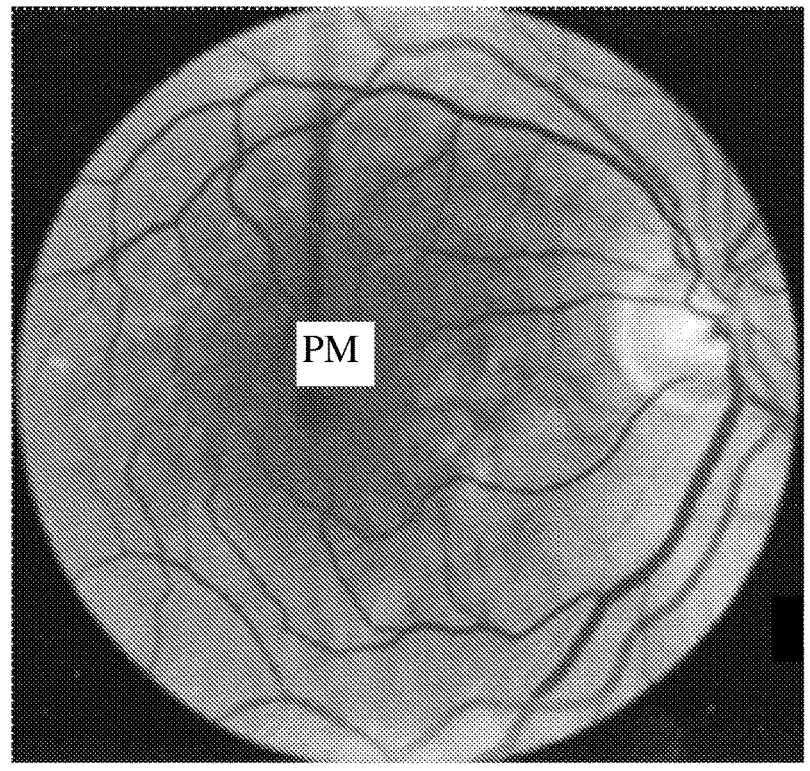
FIG. 1B(i), is a fundus image showing the same eye as shown in FIG. 1A, taken on the same day, showing fine pigmentary mottling (PM) in the macular area and a number of very fine drusen more peripherally. While shown without colour here, please refer to provisional application AU2020904628 for a colour version.
Figure 1C:
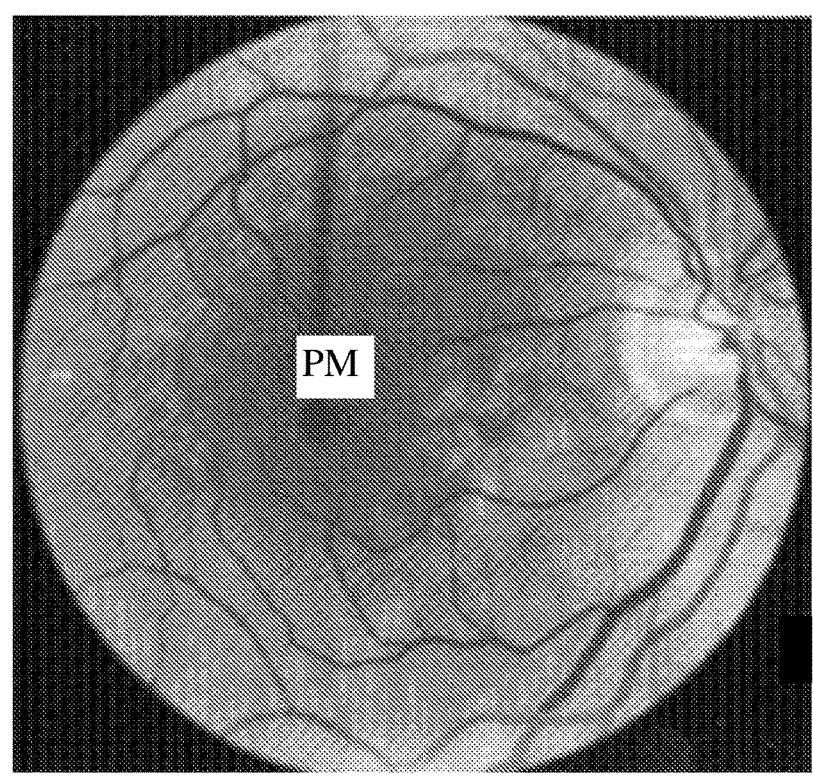
Figure 1C:
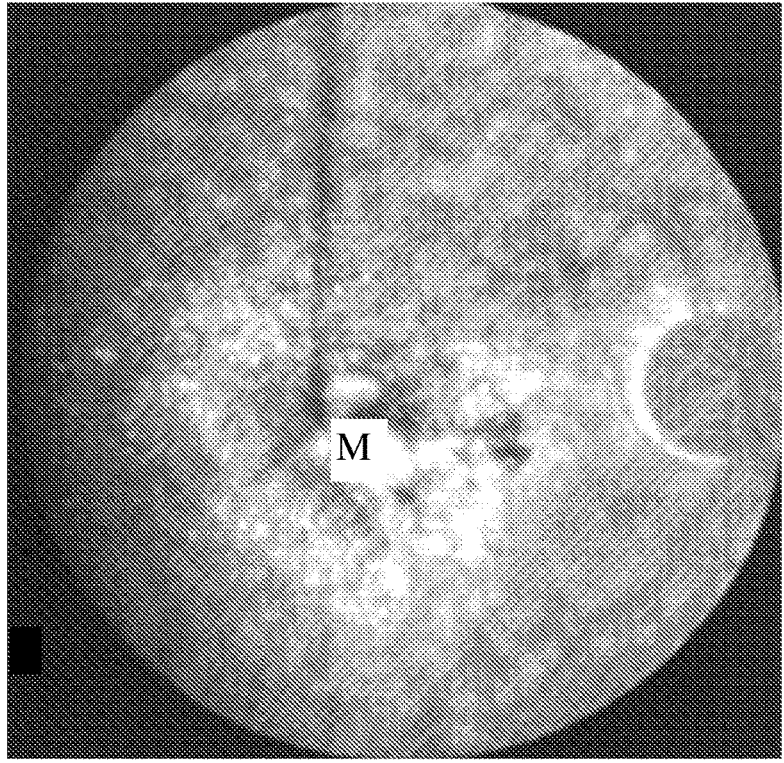
Figure 1E:
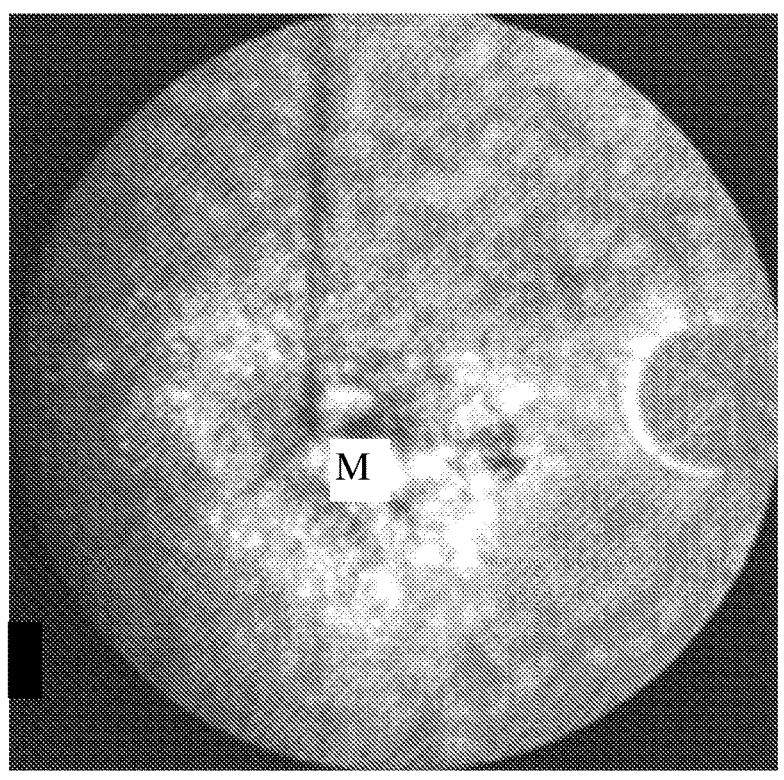
FIGS. 1E and 1F(i) are a retinal angiogram and a fundus image, respectively, of the same eye shown in FIG. 1A taken an additional two months later (i.e. four months from the date on which FIGS. 1A; 1B(i); and 1B(ii) were acquired). There has been some resolution of the haemorrhage and there is some early scarring. The angiogram shows a definite neovascular membrane (M) inferior to the fovea and extending up to the temporal side of it. While shown without colour here, please refer to provisional application AU2020904628 for a colour version of FIG. 1F(i).
Figure 1F:
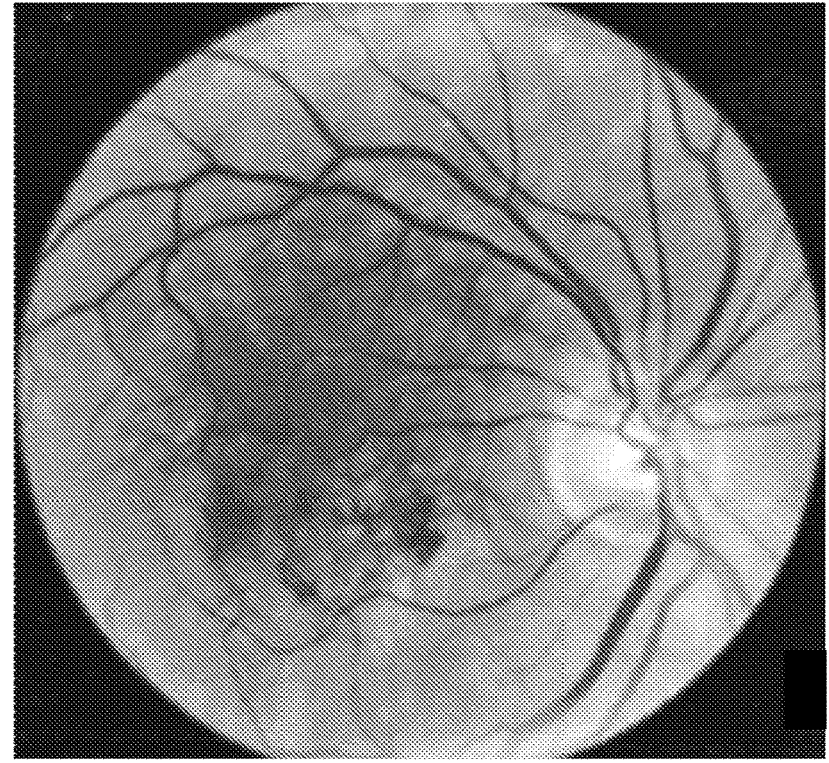

FIGS. 1A; 1B; 1C; 1D; 1E; and 1F show progression from a minor change in FIGS. 1A and 1B to a major haemorrhagic and/or neovascular legion shown in FIGS. 1E and 1F, with an intermediate stage shown in FIGS. 1C and 1D.

Figure 2A:
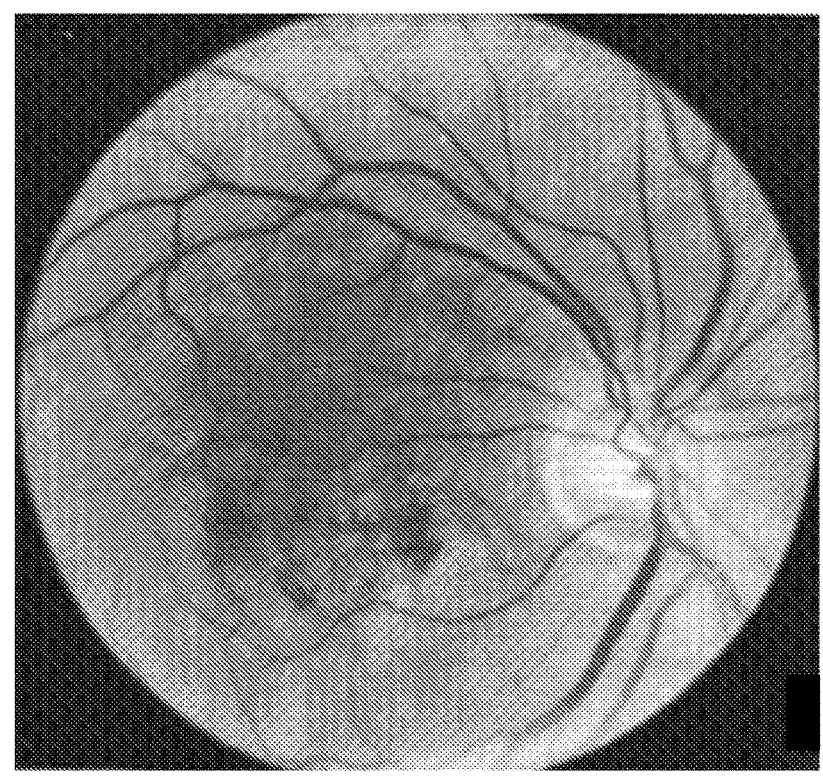
FIG. 2A(i) is a light micrograph of a toluidine blue-stained semithin section of adult retina at the fovea. The ganglion cell layer (GCL), the inner nuclear layer (INL) and the outer nuclear layer (ONL) appear well preserved, the arrangement of the inner and outer cone segments (IS, OS) is disrupted; a region of gliosis (asterisk) is present at the centre of the foveal depression, overlying pigmentary disturbance and incipient new vessels, shown at higher magnification in B. Bar 100 μm. While shown without colour here, please refer to provisional application AU2020904628 for a colour version.
Figure 2A:
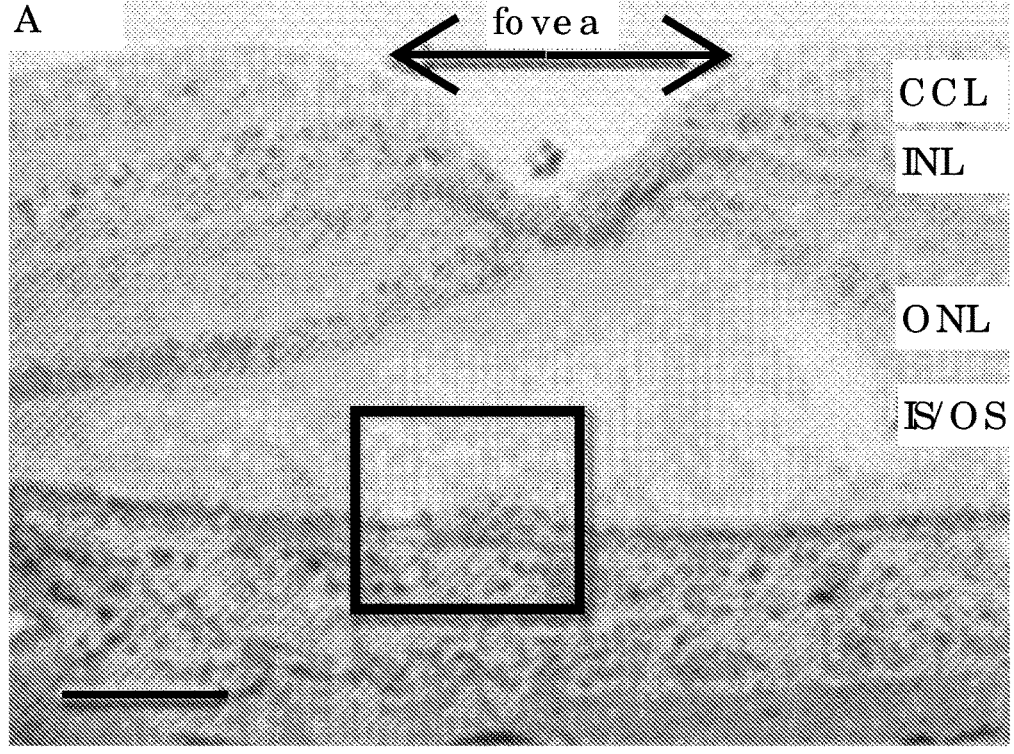
Figure 2B:
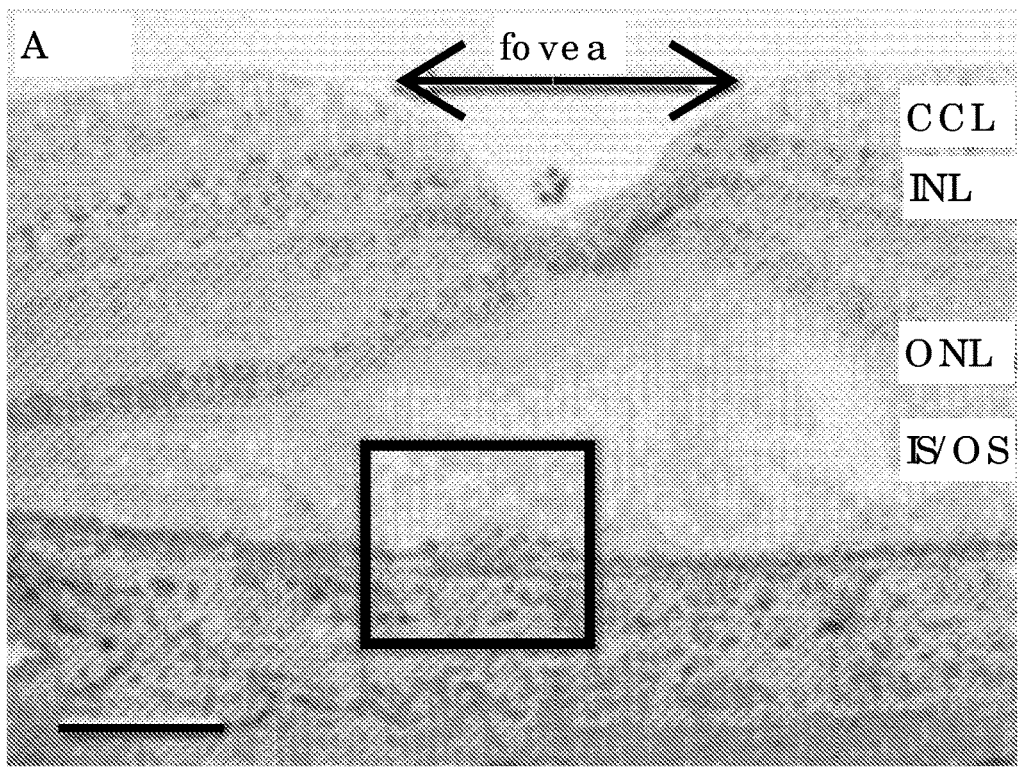
FIG. 2B(i) is the light micrograph of FIG. 2A shown at a higher magnification. Both hypo-and hyperpigmented RPE cells form a region of pigmentary disturbance (PD). Incipient new vessels (INV) are associated with increased numbers of stromal leucocytes (arrowheads) in the choroid. Bar 50 μm. While shown without colour here, please refer to provisional application AU2020904628 for a colour version.
Figure 2B:
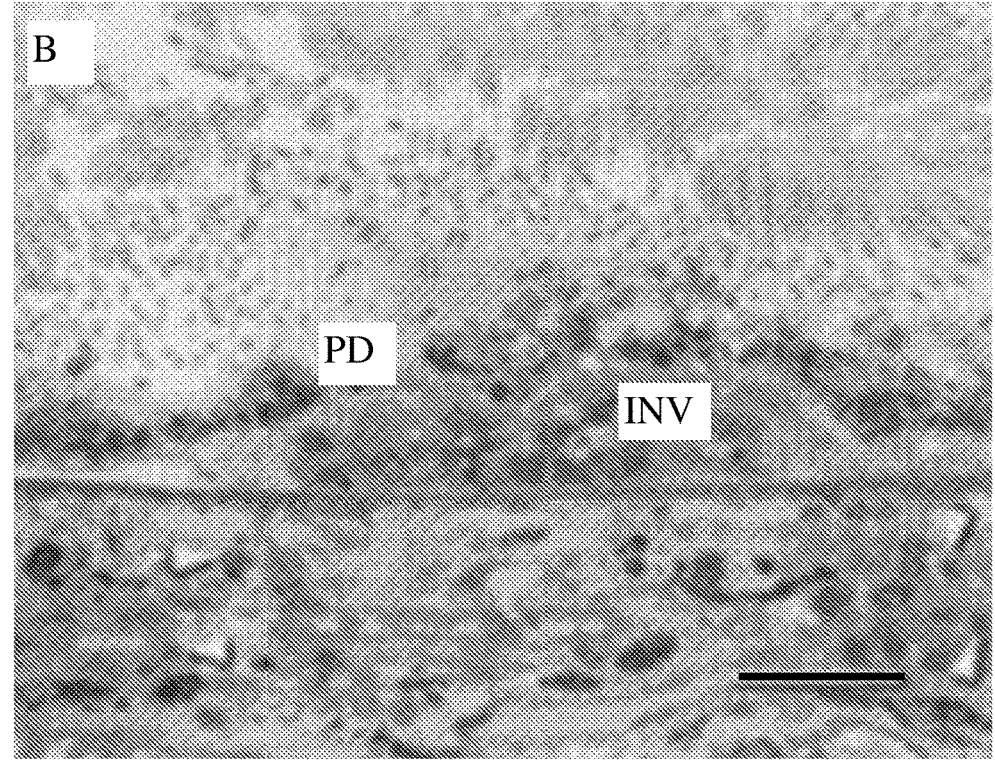
Figure 2C:
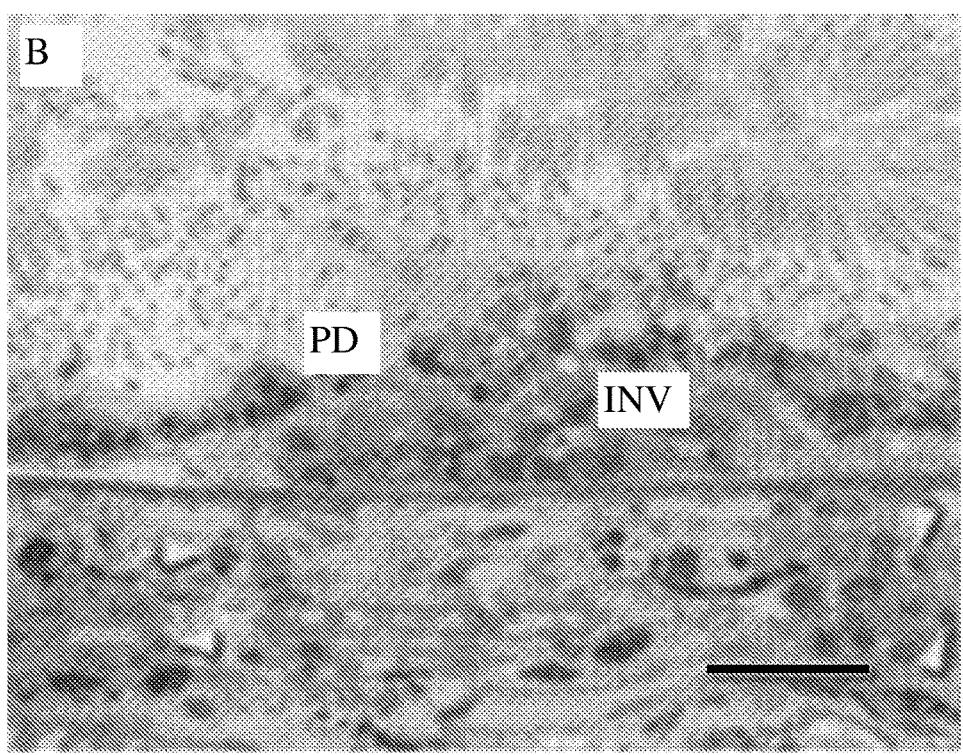
FIG. 2C is an electron micrograph taken in the region of incipient neovascularisation (A and B above) illustrating the classic morphology of a macrophage; the arrow indicates a secondary lysosome, a pseudopodium (P) is closely apposed to Bruch's membrane (BM). Bar 2.5 μm.
Figure 2C:
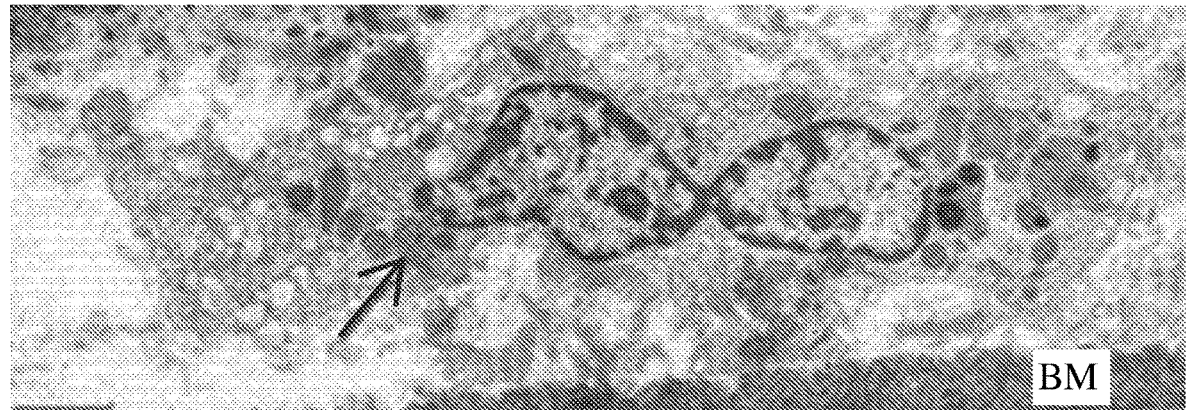

FIGS. 2A; 2B; and 2C visualises an incipient new vessel. The RPE is visible as a continuous dark line except over the new vessel where disturbance is shown. It can be seen that the RPE has lost its pigment in patches.

Either side of the fovea, there is no pigmentary disturbance. Inside the box shown in FIG. 2A, there is pigmentary disturbance. In colour figures, such as those available for viewing in the priority document, AU2020904628, the three colours we are interested in are red, black and white. If increased red, white or black in the central macula this indicates neovascularisation and thereby dry AMD.

Figures 3A, 3B:
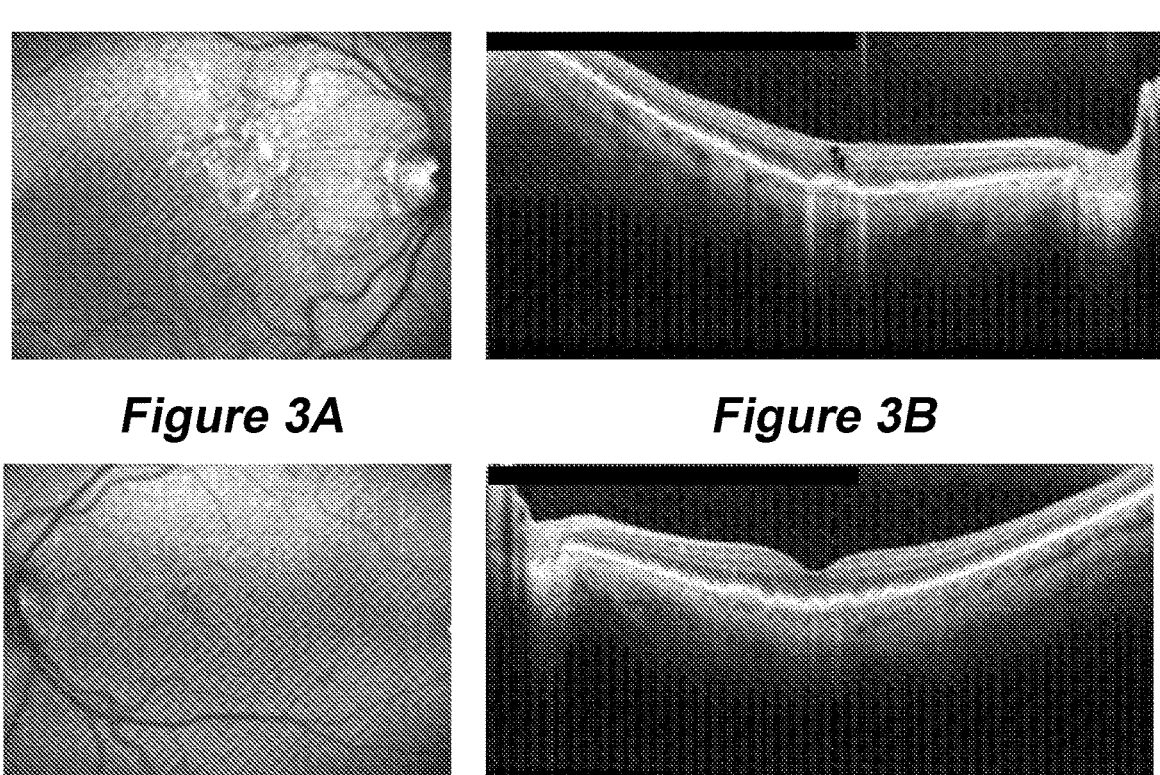
FIGS. 3A; 3B; 3C; and 3D: retinal fundus (3A) and OCT (3B) images of a patient's right eye and retinal fundus (3C) and OCT (3D) images of a patient's left eye with right wet AMD and left eye shows a mottled fundus and no apparent drusen.
Figures 3C, 3D:
Figure 4A:
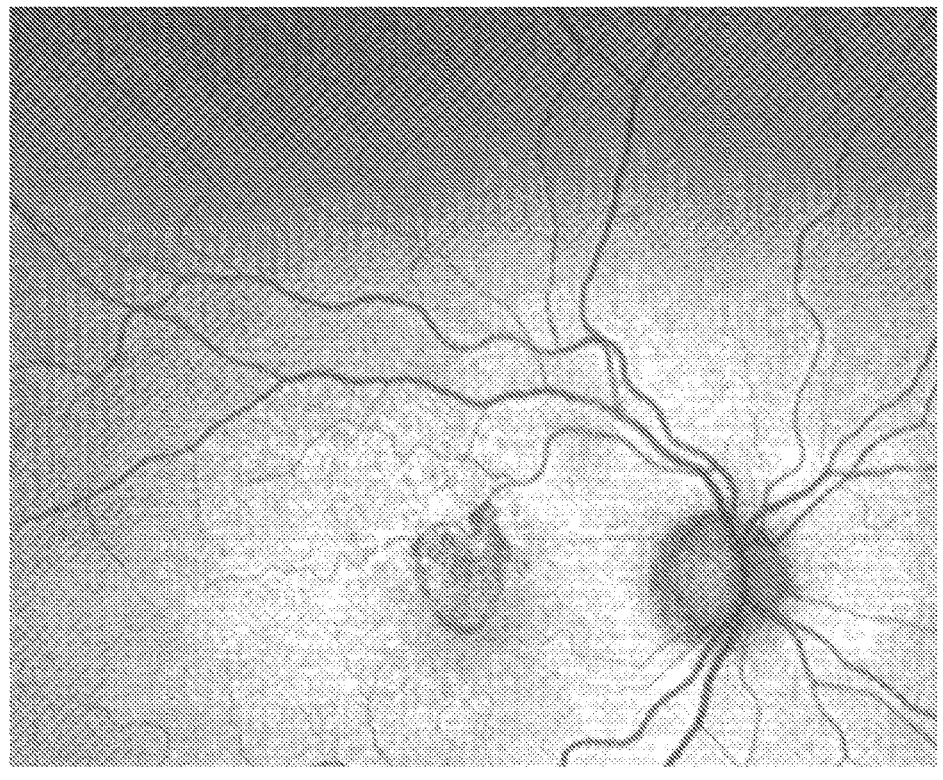
FIGS. 4A and 4B: are Optomap retinal images of the same patient as FIGS. 3A and 3B.
Figure 4B:
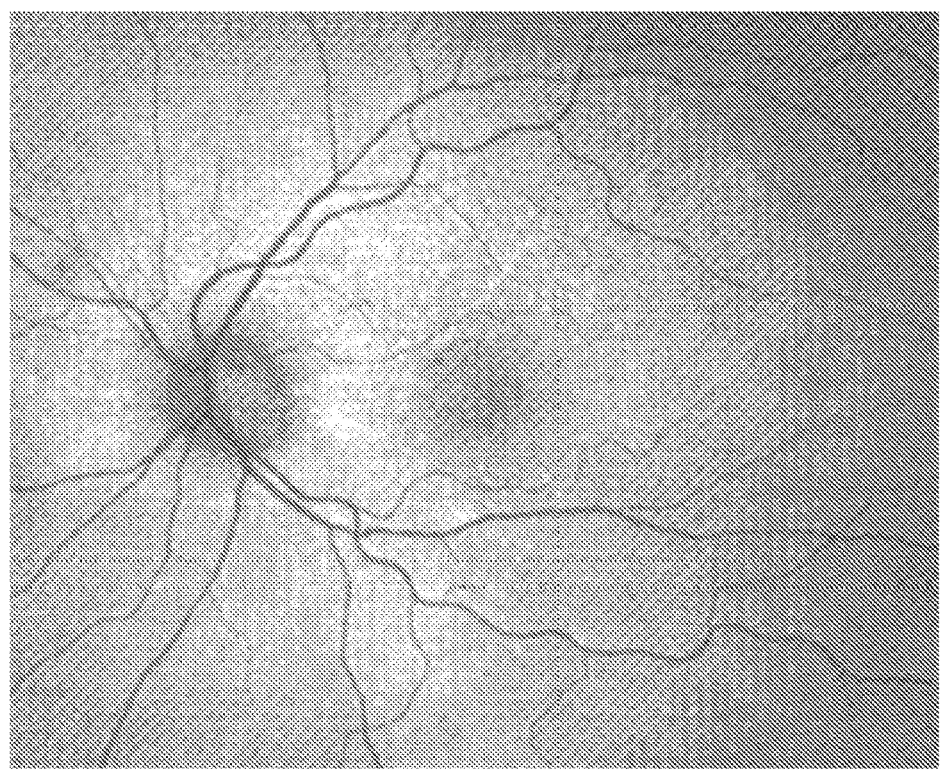
Figure 5A:
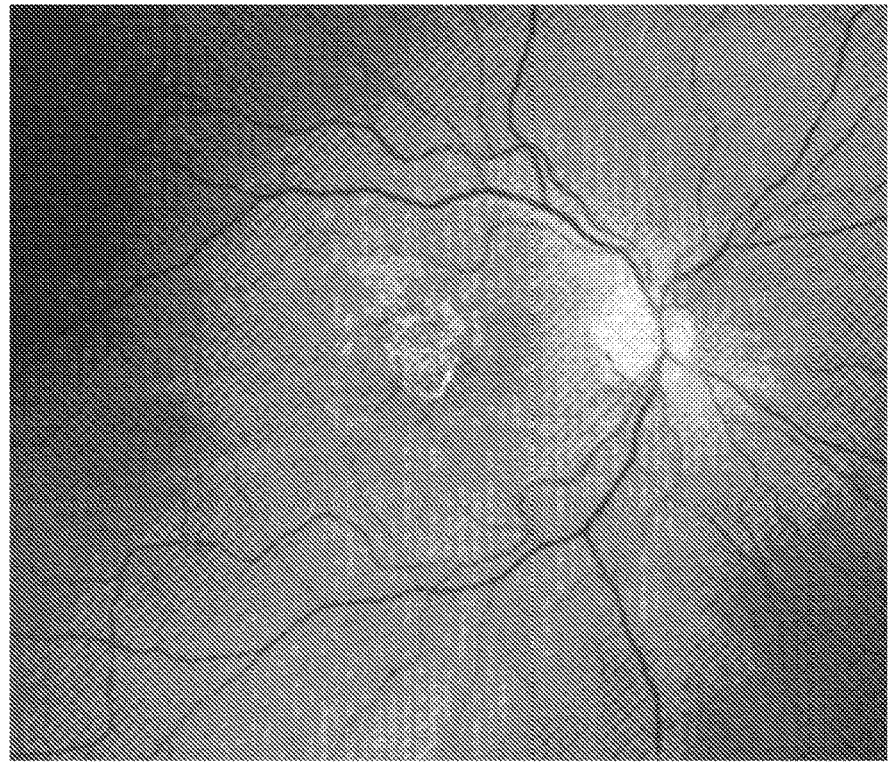
FIGS. 5A and 5B: are Optomap Fundus autofluorescence images of the same patient as FIGS. 3A and 3B.
Figure 5B:
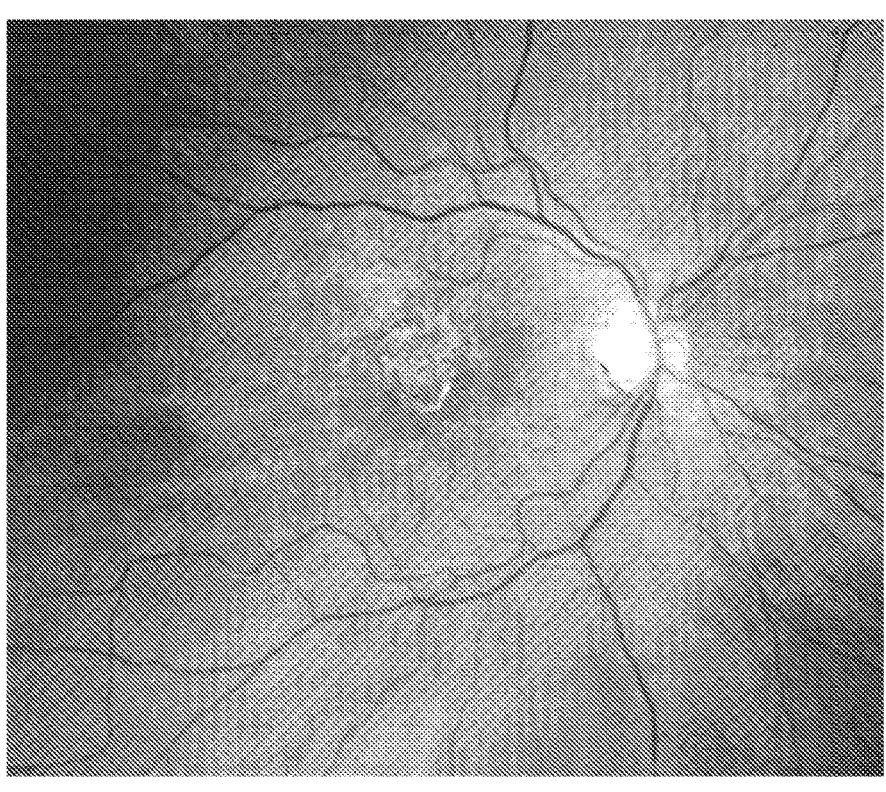
Figure 5B:

FIGS. 3; 4 and 5 are retinal images showing Right Wet AMD, being treated with Eylea injections. The Left eye shows a slight mottled fundus with no apparent drusen or neovascularization (new vessel formation). The slight mottling is exhibited as a pigmentary disturbance. VA (visual acuity) is R6/150 L6/7.5. The Left eye is at high risk of progressing to wet AMD.

When these images shown in the FIGS. 1 and 2 were obtained, it was not feasible to generate a digital image with high enough resolution or to readily access sufficient computational resources to detect the visible changes. The inventor has discovered that with advent of high resolution digital imaging and gains in computational resources, it is possible to detect these details at the micrometre level. The method, device and system of the invention can readily detect changes in the RPE due to disturbance and foci where the RPE has gone into lumps.

While ophthalmologists may be able to detect the pigmentary disturbance with their imaging techniques, the present invention allows increased sensitivity and makes the detection over time more likely. Additionally, the inventor has discovered that most people are diverted from observing the changes in the RPE by drusen. While not wanting to be bound by any one theory, the inventor hypothesises that drusen do not herald an incipient new vessel, but instead herald a new dry lesion.

Throughout the specification the aim has been to describe the invention without limiting the invention to any one embodiment or specific collection of features. Persons skilled in the relevant art may realize variations from the specific embodiments that will nonetheless fall within the scope of the invention.

The invention claimed is:

1. A method of detecting one or more change in an eye, the method comprising:
    comparing an image of the eye with at least one asynchronous image of the eye to thereby detect the one or more change in the eye wherein the change comprises a darkening or lightening in pigment of the Retinal Pigmented Epithelium (RPE) in the macula occurring in either direction from one point in time to another point in time in the form of one or both of a pigmentary disturbance and mottling.

2. The method of claim 1, wherein when the change is detected by providing a diagnosis of, indication of or predisposition to an eye disease or eye condition or a neurodegenerative disease or condition or a predisposition thereto.

3. The computer program product of claim 2, comprising:
    computer readable program code devices (ii) configured, when a change is detected, to cause the computer by one or more computer processing element to provide a diagnosis of, indication of or prognosis of an eye disease or eye condition or a neurodegenerative disease or condition or a predisposition thereto.

4. The method of claim 1, wherein the change in pigment indicates neovascularization or a new blood vessel.

5. The method, of claim 1, wherein the change is an absence of drusen or any change in drusen.

6. The method of claim 1, wherein the comparing may comprise image registration.

7. The method of claim 1, wherein the image and the at least one asynchronous image are processed.

8. The method of claim 1, wherein the comparing comprises one or more of determining intensity levels; determining a distribution of gradient magnitude; determining intensity profile.

9. The method of claim 1, wherein the change is detected by comparing intensity levels.

10. The method of claim 1, further comprising monitoring a fellow eye of a subject with neovascularisation in the other retina with the method, computer program product, device or system.

11. The method of claim 1, wherein the change may be associated with a marker of MHC class II proteins.

12. The method of claim 1, wherein the eye disease or condition comprises dry AMD.

13. The method of claim 1, wherein the treatment comprises prophylactic treatment.

14. The method of claim 1, wherein the one or more eye disease or condition comprises glaucoma.

15. The method of claim 1, wherein the eye disease and/or condition is a diabetic eye disease and/or condition.

16. The method of claim 1, wherein when the one or more change is detected, one or more mineralocorticoid and/or one or more glucocorticoid or a therapeutically active analogue, derivative, homolog, pharmaceutically acceptable salt or conjugate thereof is applied to the eye.

17. The method of claim 1, wherein when the one or more change is detected, a treatment with hemp, hemp oil or a pharmaceutically effective extract is applied.

18. The method of claim 1, wherein the eye disease or condition comprises age related maculopathy or wet age related maculopathy.

19. A computer program product comprising a nontransitory computer useable medium said computer program product comprising:

a computer usable medium and computer readable program code embodied on said computer usable medium for detecting one or more change in an eye, the computer readable code comprising:

computer readable program code devices (i) configured to cause the computer to compare by one or more computer processing element an image of the eye with at least one asynchronous image of the eye to thereby detect the one or more change in the eye wherein the change comprises a darkening or lightening in pigment of the Retinal Pigmented Epithelium (RPE) and/or macula occurring in either direction from one point in time to another point in time in the form of one or both of a pigmentary disturbance or mottling.

20. A device for detecting one or more change in an eye, the device comprising:

a processor for comparing an image of the eye with at least one asynchronous image of the eye to thereby detect the one or more change in the eye wherein the change comprises a darkening or lightening in pigment of the Retinal Pigmented Epithelium (RPE) and/or macula occurring in either direction from one point in time to another point in time in the form of one or both of a pigmentary disturbance and mottling.

21. The device of claim 20, wherein when a change is detected by providing a diagnosis of, indication of or predisposition to an eye disease or eye condition or a neurodegenerative disease or condition or a predisposition thereto.

\* \* \* \* \*